US009617330B2

(12) United States Patent
Kang et al.

(10) Patent No.: US 9,617,330 B2
(45) Date of Patent: Apr. 11, 2017

(54) CHEMOREPULSION OF CELLS

(75) Inventors: Hyun Kang, Belmont, MA (US); Scott Sacane, Weston, CT (US); Jonathan L. Moon, Decatur, GA (US); Erica B. Goodhew, Atlanta, GA (US); Lopa Bhatt, Roswell, GA (US); Stacey L. Rose, Atlanta, GA (US); Milton H. Werner, Marietta, GA (US)

(73) Assignee: Celtaxsys, Inc., Atlanta, GA (US)

( * ) Notice: Subject to any disclaimer, the term of this patent is extended or adjusted under 35 U.S.C. 154(b) by 1268 days.

(21) Appl. No.: 12/698,732

(22) Filed: Feb. 2, 2010

(65) Prior Publication Data
US 2010/0203087 A1    Aug. 12, 2010

Related U.S. Application Data

(62) Division of application No. 11/867,290, filed on Oct. 4, 2007, now abandoned.

(60) Provisional application No. 60/850,070, filed on Oct. 6, 2006.

(51) Int. Cl.
| A61K 38/17 | (2006.01) |
| C07K 16/18 | (2006.01) |
| A61K 31/045 | (2006.01) |
| A61K 31/337 | (2006.01) |
| A61K 31/352 | (2006.01) |
| A61K 31/739 | (2006.01) |
| G01N 33/50 | (2006.01) |
| A61K 38/57 | (2006.01) |

(52) U.S. Cl.
CPC ............ *C07K 16/18* (2013.01); *A61K 31/045* (2013.01); *A61K 31/337* (2013.01); *A61K 31/352* (2013.01); *A61K 31/739* (2013.01); *A61K 38/1709* (2013.01); *A61K 38/1719* (2013.01); *A61K 38/1732* (2013.01); *A61K 38/57* (2013.01); *G01N 33/5029* (2013.01); *C07K 2317/76* (2013.01)

(58) Field of Classification Search
None
See application file for complete search history.

(56) References Cited

U.S. PATENT DOCUMENTS

| 5,252,557 | A |   | 10/1993 | Kita et al. |
| 5,514,555 | A |   | 5/1996  | Springer et al. |
| 5,843,705 | A |   | 12/1998 | DiTullio et al. |
| 5,948,628 | A | * | 9/1999  | Cummings et al. ......... 435/7.24 |
| 6,967,021 | B2 | * | 11/2005 | Panjwani et al. .......... 424/185.1 |
| 7,186,681 | B2 |   | 3/2007  | Liu et al. |
| 7,919,097 | B2 | * | 4/2011  | Groen et al. ............... 424/184.1 |
| 8,377,914 | B2 | * | 2/2013  | Goodhew ............ A61K 31/122 |
|           |    |   |         | 514/167 |
| 8,715,654 | B2 | * | 5/2014  | Chavan ................. C07K 16/30 |
|           |    |   |         | 424/130.1 |
| 9,050,352 | B2 | * | 6/2015  | Ralph ................ A61K 31/7016 |
| 2004/0229778 | A1 |   | 11/2004 | Elmaleh et al. |
| 2004/0229795 | A1 |   | 11/2004 | Roemisch et al. |
| 2005/0048574 | A1 |   | 3/2005  | Kantor et al. |
| 2006/0148712 | A1 |   | 7/2006  | Liu et al. |
| 2007/0134657 | A1 |   | 6/2007  | Poznansky et al. |

FOREIGN PATENT DOCUMENTS

| WO | 9912041 A1   | 3/1999  |
| WO | 00/59941 A1  | 10/2000 |
| WO | 2005009350 A2 | 2/2005 |

OTHER PUBLICATIONS

Kasai et al., Journal of Biochemistry, 119:1-8, 1996.*
Thompson et al., Journal of Immunology, 165:426-34, 2000.*
Dell'Aica, I., et al., "Matrix proteases, green tea, and St. John's wort: biomedical research catches up with folk medicine," Clinica Chimica Acta, 381:69-77, 2007.
Dell'Aica, et al., "Hyperforin blocks neutrophil activation of matrix metalloproteinase-9, motility and recruitment, and restrains inflammation-triggered angiogenesis and lung fibrosis," J. Pharmacol. Exp. Ther., 321(2):492-500, 2007.
Penno, M. B., et al., "Rapid and Quantitative in Vitro Measurement of Cellular Chemotaxis and Invasion," Methods in Cell Sciebce, 19: 189-195, 1997.
Lepelletier, Y., et al., "Control of human thymocyte migration by Neuropilin-1/Semaphorin-3A-mediated interactions," PNAS, 104(13): 5545-5550, 2007.
Holmes, S., et al., "Sema7A is a Potent Monocyte Stimulator," Scand. J. Immunol., 56: 270-275, 2002.
Vacca, A., et al., "Loss of inhibitory semaphorin 3A (SEMA3A) autocrine loops in bone marrow endothelial cells of patients with multiple myeloma," Blood, 108(5): 1661-1667, 2006.
Barberis, D., et al., p190 Rho-GTPase activating protein associates with plexins and it is required for semaphorin signalling, J. Cell Sci., 118: 4689-4700, 2005.
Papeta, N., et al., "Long-term Survival of Transplanted Allogeneic Cells engineered to Express a T Cell Chemorepellent," Transplantation, 83(2): 174-183, 2007.
Poznansky, M. C., et al., "Active movement of T cells away from a chemokine," Nature Medicine, 6(5): 543-548, 2000.
Bielenberg, D. R., et al., "Semaphorin 3F, a chemorepulsant for endothelial cells, induces a poorly vascularized, encapsulated, nonmetastatic tumor phenotype," The Journal of Clinical Investigation, 114(9): 1260-1271, 2004.
Sabroe, I., et al., "The Role of Toll-Like Receptors in the Regulation of Neutrophil Migration, Activation, and Apoptosis," Clinical Infectious Diseases, 41: S421-S426, 2005.
Ogilvie, P., et al., "Eotaxin is a natural antagonist for CCR2 and an agonist for CCR5," Blood, 97(7): 1920-1924, 2001.
Zlatopolskiy, A., et al., "'Reverse Gear' Cellular Movement Mediated by Chemokines," Immunology and Cell Biology, 79: 340-344 (2001).

(Continued)

*Primary Examiner* — Marianne P Allen
(74) *Attorney, Agent, or Firm* — Elmore Patent Law Group, P.C.; Mahreen Chaudhry Hoda; Carolyn S. Elmore, Esq.

(57) ABSTRACT

The present invention provides compositions and methods of controlling the direction and/or movement of migratory cells. Specifically, the invention is directed to the identification of novel chemorepellents and unimodal fugetaxins, their agonists and antagonists which alter or affect the movement of cells involved in immune, inflammatory or cancerous phenotypes.

2 Claims, 9 Drawing Sheets

(56) References Cited

OTHER PUBLICATIONS

Goshima, Y., et al., "Semaphorins as signals for cell repulsion and invasion," The Journal of Clinical Investigation, 109(8): 993-998, 2002.
Lauffenburger, D. A., et al., "Chemotactic Factor Concentration Gradients in Chemotaxis Assay Systems," Journal of Immunological Methods, 40: 45-60, 1981.
Schratl, P., et al., "Hierarchy of eosinophil chemoattractants: role of p38 mitogen-activated protein kinase," European Journal of Immunology, 36: 2401-2409, 2006.
Rozell, M. D., et al., "Isolation technique alters eosinophil migration response to IL-8," Journal of Immunological Methods, 197: 97-107, 1996.
Ishihara, K., et al., "Mechanism of the Eosinophilic Differentiation of HL-60 Clone 15 Cells Induced by n-Butyrate," International Archives of Allergy and Immunology, 137(Suppl. 1): 77-82, 2005.
Kaneider, et al. (2002). Syndecan-4 mediates anthithrombin-induced chemotaxis of human peripheral blood lymphocytes, Journal of Cell Science, 115(1): 227-236.
Yamashiro, et al. (2001). Inhibitory effects of antithrombin III against leukocyte rolling and infiltration during endotoxin-Investigative Opthamology & Visual Science 42(7):1553-1560.
Elmaleh, et al. (2005). Antiviral activity of human antithrombin III. International Journal of Molecular Medicine 16(2): 191-200.
Kaneider, et al. (2002). Inhibition of human neutrophil chemotaxis toward interleukin 8 with six clinical antithrombin concentrates in vitro. Intensive Care Med 28: 1447-1452.
Ostrovsky, et al. (1997). Antithrombin III prevents and rapidly reverses leukocyte recruitment in Ischemia/Reperfusion. Circulation 96: 2302-2310.
Kaneider, et al. (2001). Distinct antithrombin III preparations deactivate IL-8 induced neutrophil chemotaxis with different potency. Meeting abstract. Critical Care 5(Suppl 1): 102.
Vianello, F., et al., "Fugetaxis: active movement of leukocytes away from a chemokinetic agent", Journal of Molecular Medicine, 83(10): 752-763 (2005).
Lewis, M.G., et al., "Immune Derangement in Patients with Malignant Melanoma," J. Cutaneous Pathology, 6: 201-207, 1979.
O'Leary, E.C., et al., "Glucocorticoid-mediated Inhibition of Neutrophil Migration in an Endotoxin-induced Rat Pulmonary Inflammation Model Occurs Without an Effect on Airways MIP-2 Levels," Am. J. Resp. Cell Mol. Bio., 16: 267-274, 1997.
La, M., et al., "Effect of Galectin-1 on Neutropiiil Chemotaxis In Vitro and Migration In Vivo," Brit. J. Pharmacol., 135, Suppl. p. 160P (2002).
Almkvist, J., et al., "Galectins as inflammatory mediators," Glycoconjugate J., 19: 575-581 (2004).
Yamaguchi, M. A., et al., "Heparin and Antithrombin III Inhibited Neutrophil Adhesion to Endotoxin-activated Vascular Endothelial Cells," Myakkan-gaku (Angiology), 39(4): 189-194 (1999).
Ishii, H., "Immunohistochemical expression of cyclooxygenase-2 and heat shock protein 25 in synovial lining cells in the rat temporomandibular joint subjected to long-period of forcible opening," Tsurumi Shi-gaku (School of Dental Medicine of Tsurumi University), 30(1): 31-40 (2004).
Abstracts-4 of Speech of The Pharmaceutical Society of Japan 122nd annual meeting, p. 28 (2002). http://medproc.tokyojst.go.jp/yokou/disp/JYDetailJd2.jspjsessionid=006F8364A . . . (2002).
Sugihara, E., "Effect of Macrolide Antibiotics on Neutrophil Function in Human Peripheral Blood," Kansenshou-gaku Zassi (Review Journal of Infectious Disease Medicine), 71(4): 329-336 (1997).
Walzer, T. et al., "Poxvirus semaphorin A39R inhibits phagocytosis by dendritic cells and neutrophils," Eur.J. Immunol., 35: 391-398 (2005).
Wiedow, O., et al., "Elafin Is a Potent Inhibitor of Proteinase 3," Biochemical and Biophysical Research Communications, 174(1): 6-10 (1991).
Rowand, et al. "Hirudin C—Terminal Fragments Inhibit Thrombin Induced Neutrophil Chemotaxis," Thrombosis and Haemostasis, 67(3):289-291 (1992).
Dunzendorfer, et al. "Cell-surface heparan sulfate proteoglycan-mediated regulation of human neutrophil migration by the serpin antithrombin III," Blood, 97(4):1079-1085 (2001).
Saito, Hajime, et al., Effect of antithrombin III on neutrophil deformability, Journal of Leukocyte Biology, Sep. 2005, vol. 78, pp. 777-784.

\* cited by examiner

CHEMOREPULSION OF CELLS

RELATED APPLICATIONS

This application is a divisional of U.S. application Ser. No. 11/867,290, filed Oct. 4, 2007, which claims the benefit of U.S. Provisional Application No. 60/850,070, filed on Oct. 6, 2006. The entire teachings of the above applications are incorporated herein by reference.

BACKGROUND OF THE INVENTION

Chemotaxis, or the oriented movement of a cell with reference to a chemical agent is a complex and highly integrated process. The movement may be positive (toward) or negative (away) with respect to the chemical gradient. Once triggered, this process in turn mediates, among many things, tissue organization, organogenesis and homeostasis and ultimately orchestrates embryonic morphogenesis; contributes to tissue repair and regeneration; and drives disease progression in cancer, mental retardation, atherosclerosis, and arthritis. The migrating cell is highly polarized with complex regulatory pathways that spatially and temporally integrate its component processes.

Chemotaxis occurs in both prokaryotes and eukaryotes. In all cases, movement toward an agent or stimulus is termed positive chemotaxis (i.e., the agent or stimulus is chemoattractive for the cell), while movement away from an agent or stimulus is termed negative chemotaxis (i.e., the agent or stimulus is chemorepulsive for the cell). Chemoattraction (CA) and chemorepulsion (CR) are therefore properties of the agent or stimulus, while chemotaxis is a property of cells.

It is believed that for both prokaryotes and eukaryotes, cells undergoing chemotaxis sense a change in agent concentration and, thereby, move along a concentration gradient.

Chemotaxis is known to occur for several types of eukaryotic cells. Within the immune system, chemotaxis is often driven by a class of biological agents, known as chemokines (or chemotactic cytokine).

Chemotaxis, and the related phenomenon, chemokinesis (the enhancement of random cellular movement in response to a chemical or biological agent, irrespective of agent concentration), have been examined in subpopulations of mammalian cells. Chemorepulsion, however, has rarely been described as a physiological phenomenon. In one instance, the chemokine SDF-1 (a.k.a. SDF-1α, CXCL12) has been described as a chemorepellent in the context of a two-dimensional transmigration apparatus and at a concentration 10-fold above that necessary for the induction of chemoattraction in the same device. Observationally, the response allegedly induced by SDF-1, termed "fugetaxis," appears to be analogous to chemorepulsion, as the latter term is known in the art. However, it is not clear whether "fugetaxis" is truly different from chemorepulsion.

Moreover, chemorepulsion of immune cells in response to non-chemokine biological or chemical agents has never been described.

A thorough understanding of the mechanisms underlying cell migration will facilitate development of therapies for the treatment of cell migration-related disorders.

SUMMARY OF THE INVENTION

The present invention provides methods of controlling the direction and/or movement of migratory cells, or cell migration. Disclosed herein are chemorepellents, including non-chemokines, which have not previously been identified in the art as chemorepellents.

In another embodiment is disclosed a method of identifying and validating chemokine and non-chemokine agents as chemorepellents.

According to another aspect of the invention, a method for identifying cells which secrete a chemorepulsive agent is provided.

In another embodiment, the invention is directed to the identification of unimodal fugetaxins which alter or affect the movement of primary cells involved in immune, inflammatory or cancerous phenotypes.

According to another aspect of the invention, a method of modulating migration of immune cells is provided. Modulation may be toward or away from a particular location or site in an animal or subject.

According to another aspect of the invention, a high throughput transmigration assay method of screening for chemorepellent agents is provided. This method generally involves contacting an agent suspected of being a chemorepellent with a cell capable of induced migration, measuring the movement of the cell, wherein movement of the cell away from the agent is indicative of chemorepulsion.

According to another aspect of the invention, a method of inhibiting endothelial cell migration to a tumor site in a subject is provided. The method involves locally administering to an area surrounding a tumor site in need of such treatment a validated chemorepellent in an amount effective to inhibit endothelial cell migration to the tumor site in the subject. In certain embodiments, the area surrounding the tumor site is not immediate to the tumor site.

According to one aspect of the invention, a method of inhibiting tumor cell metastasis in a subject is provided. The method involves contacting or administering, either locally or systemically, to a tumor site in a subject in need of such treatment a validated chemorepellent agonist or antagonist agent in an amount effective to inhibit metastasis of tumor cells from the tumor site in the subject.

These and other aspects of the invention, as well as various advantages and utilities, will be more apparent with reference to the drawings and the detailed description of the embodiments of the invention.

DETAILED DESCRIPTION OF THE INVENTION

Figure 1A:
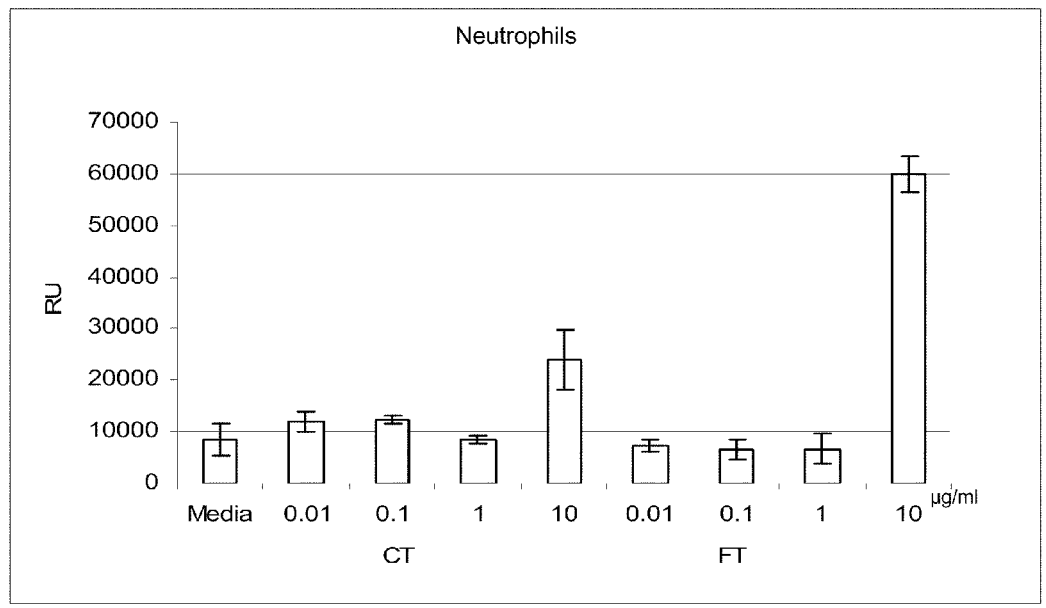
FIGS. 1A-C are bar graphs of the chemotactic response of neutrophils and lymphocytes to galectin-3.

A description of the embodiments of the invention follows.

The present invention involves the unexpected discovery of agents which can act as chemorepellents, most of which are not related to chemokines or other proteins whose actions are mediated by GPCRs. The newly-discovered chemorepellents also include agents that are of chemokine origin and yet not previously recognized as chemorepellents. In addition to novel chemorepellents, applicants have further identified several unimodal fugetaxins.

Also disclosed herein are methods of identifying chemorepellents as well as agonizing and antagonizing their effects on migratory cells, pharmaceutical compositions comprising chemorepellents and an assay for the identification of cells which secrete chemorepellents.

The object of the present invention is to identify and/or isolate agents which induce, elicit or trigger human migratory cells to move in a desired direction. By "desired direction" is meant in any direction whether away from or toward a site or location, whereby the movement is therapeutically relevant as contributing to the improving, lessening, ameliorating, preventing, treating or mitigating a disease state or condition. The migratory cells of most interest include those involved in the process of cancer, immunity or inflammation but may include those identified to play a role in any disease state or condition.

Chemorepellents

A "chemorepellent" is an agent or stimulus which induces, elicits or triggers negative chemotaxis (movement away from an agent or stimulus) in a migratory eukaryotic cell. As used herein the terms "induce", "elicit" and "trigger," when referring to the chemorepulsive activity of a chemorepellent, carry the same meaning Chemorepellents are said to effect "chemorepulsion" or to have "chemorepulsive activity." A "validated chemorepellent" is an agent which exhibits a repellent index equal to or greater than 1.2 over at least a 10-fold change in concentration. The "Repellent Index" (RI) is a measure of the ability of an agent to induce chemorepulsion of a cell relative to any spontaneous movement the cell might exhibit. An agent's repellent index is the ratio of chemorepulsion (CR) to spontaneous migration (SM), i.e., [(CR)/(SM)]. Spontaneous migration is the amount of migration which occurs in the absence of an added agent.

As used herein, the term "agent" refers generally to any compound. Such compounds in the context of the present invention may be those having suspected chemorepulsive activity or may be a known compound such as a drug or other therapeutic substance. Agents may also be agonists or antagonists of chemorepellents, validated chemorepellents or validated conditioned chemorepellents.

As used herein the term "stimulus" refers to any physical or chemical cue that provokes or evokes a response in a system. As such, an agent may also act as a stimulus.

The chemorepellents identified using the methods of the present invention may upon contact with a migratory cell act to spatially or temporally modulate cell migration. As used herein, the terms "contact" or "contacting" means the act of touching or bringing together two entities or things in such proximity as will allow an influence of at least one on the other. The definition, while inclusive of physical contact is not so limited.

As used herein, the phrase "spatially modulating cell migration" refers to altering the movement of a cell or population of like cells in reference to a certain locality in a subject, especially in reference to the location of a cell or cells in a subject in relation to a the location of the same cell or cells in the subject after the movement.

As used herein, the phrase "temporally modulating cell migration" refers to altering the movement of a cell or population of like cells over the passage of time, especially in reference to the rate a cell or cells are induced to move.

The agents identified and/or validated as chemorepellents according to the present invention may act to effect chemorepulsion by any pathway or mechanism. The agents may bind to a surface receptor. Surface receptors include but are not limited to G-protein coupled receptors; Toll-like receptors, cytokine and chemokine receptors, T-cell receptors, neuropilin receptors, tumor necrosis factor receptors, growth factor receptors, ion channels, ion pumps and porins.

The agents may be internalized once bound or may remain on the surface of the cell.

The agents may interact with a substance or biologic factor in the intercellular milieu, such as second messengers or soluble ligands, which then go on to translate the chemorepellent effects to the cell whose movement is being affected.

Chemorepulsive activity can be detected using any of the transmigration systems, including the high throughput transmigration assay described herein (see Examples). It is also possible to use a variety of other systems well known in the art (e.g. U.S. Pat. No. 5,514,555, "Assays and therapeutic methods based on lymphocyte chemoattractants").

Sources of Chemorepellents

Chemorepellants may be identified from a variety of cells, including cultured homogeneous and heterogeneous cell populations which in turn may be derived from a variety of sources. Cells can be of any type or origin. Chemorepellents may be isolated from cells of healthy or diseased tissue. As used herein "diseased tissues or organs" include those tissue or organs which have or are suspected of having an impairment of health or a condition of abnormal functioning. Chemorepellents may also be isolated from or used to treat conditions associated with an immune privileged tissue. An "immune-privileged" tissue is a tissue with immune-cell tolerance and includes, but is not limited to, brain tissue, central nervous system tissue, testes, eyes or placenta.

The chemorepellents can also be isolated from one or more biological fluids. Biological fluids include, but are not limited to, synovial fluid, cerebrospinal fluid, fallopian tube fluid, seminal fluid, ocular fluid, pericardial fluid, pleural fluid, inflammatory exudates, eluates, lysates and ascitic fluid. It is also appreciated that any migratory cell as disclosed herein may also be the source of chemorepellents.

Migratory Cells

As used herein, "migratory cells" are those cells which are capable of movement from one place to another in response to a stimulus. Preferred types of cells whose migration is to be mediated by the identified and/or validated chemorepellents of the present invention include, but are not limited to immune cells including, monocytes, Natural Killer (NK) cells, dendritic cells (which could be immature or mature), subsets of dendritic cells including myeloid, plasmacytoid (also called lymphoid) or langerhans; macrophages such as histiocytes, Kupffer's cells, alveolar macrophages or peritoneal macrophages; neutrophils, eosinophils, mast cells, basophils; B cells including plasma B cells, memory B cells, B-1 cells, B-2 cells; CD45RO (naive T), CD45RA (memory T); CD4 Helper T Cells including Th1, Th2 and Tr1/Th3; CD8 Cytotoxic T Cells, Regulatory T Cells and Gamma Delta T Cells.

Cells may readily be derived from a number of appropriate organs or tissues including, but not limited to, skin, liver, pancreas, fat, bone marrow, lymph node, thymus, kidney, colon, and brain.

Cells may be of "hematopoietic origin" and include, but are not limited to, pluripotent stem cells, multipotent progenitor cells and/or progenitor cells committed to specific hematopoietic lineages. The progenitor cells committed to specific hematopoietic lineages may be of T cell lineage, B cell lineage, dendritic cell lineage, neutrophil lineage, Langerhans cell lineage and/or lymphoid tissue-specific macrophage cell lineage. The hematopoietic cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, the "hematopoietic origin" cells may be derived from in vitro cultures of any of the foregoing cells, and in particular in vitro cultures of progenitor cells.

Cells of neural origin include neurons and glia, and/or cells of both central and peripheral nervous tissue.

Cells of epithelial origin, include cells of a tissue that covers and lines the free surfaces of the body. Such epithelial tissue includes cells of the skin and sensory organs, as well as the specialized cells lining the blood vessels, gastrointestinal tract, air passages, lungs, ducts of the kidneys and endocrine organs.

Cells of mesenchymal origin include cells that express typical fibroblast markers such as collagen, vimentin and fibronectin.

Cells involved in angiogenesis are cells that are involved in blood vessel formation and include cells of endothelial origin and cells of mesenchymal origin.

A germ cell is a cell specialized to produce haploid gametes. It is a cell further differentiated than a stem cell, which can still give rise to more differentiated germ-line cells.

According to the present invention, a method is provided to identify chemorepellents which are isolated from a serum-free conditioned media. Conditioned media include, but are not limited to, any serum-free growth medium in which a cell that secretes a chemorepellent has been grown or maintained for at least 24 hours; an ascites fluid collected from a patient with cancer; a lysate of cells in which a chemorepellent has been expressed or synthesized or other biological fluid. Biological fluids include, but are not limited to, synovial fluid, cerebral spinal fluid, fallopian tube fluid, ocular fluid, pericardial fluid, pleural fluid or inflammatory exudates. The chemorepellent can be isolated from a non-homogeneous solution derived from a cell culture supernatant, also known as a cell culture conditioned media. On a small scale, a conditioned medium can be contained in culture flasks, plates and dishes. On a larger scale, culture vessels such as fermenters can be used. Culturing in three-dimensional porous matrices can also be used. In all embodiments, the chemorepellent present in the conditioned medium can be removed centrifugation of the cell culture to remove the cells and aspiration to recover the solution in which the cells were bathed. The cultures can also be filtered to remove cells and cell debris. The chemorepellent in the conditioned medium can be fractionated according to standard chromatographic procedures to facilitate isolation of the chemorepellent. One with ordinary skill in the art will be familiar with such procedures that include, but are not limited to, size exclusion chromatography, FPLC, HPLC, ion-exchange chromatography, hydrophobic chromatography, immune-affinity chromatography, etc.

In preferred embodiments, the fractions of conditioned media are then used to repel immune cells.

According to another aspect of the invention, a method for identifying cells which secrete a chemorepulsive agent is provided. The method involves preparing a culture of mammalian cells derived from tumors or other diseased state or a culture of bacterial, viral or fungal cells and isolating a supernatant suspected of containing a chemorepellent agent from the culture, fractionating the supernatant into a plurality of fractions with chemorepulsion activity and measuring the movement of cells away from a fraction. In any of the foregoing embodiments, the plurality of fractions may be undiluted or concentrated. The cell secretions may contain one or more putative chemorepellents and may be a mixture, aliquot or pooled fraction therefrom.

The agent isolated from a positive fraction can be further characterized by subjecting the fraction to protein sequencing according to standard methods or mass spectrometry coupled with chemical or electrochemical fragmentation. Any chemical information so obtained can be screened with databases for homology to existing proteins, polypeptides, carbohydrates, lipids, or combinations thereof. Alternatively, a positive fraction can be used to generate antibodies, which recognize the chemorepellent. Such antibodies can then be used in expression cloning protocols, Western blots, and other techniques useful in the isolation of chemorepellents from a conditioned medium.

In other embodiments, the chemorepellent is present in a tumor cell culture supernatant, tumor cell eluate and/or tumor cell lysate. The tumor cell may be of a cancer or tumor type that is thought to escape immune recognition.

Such cancers can be of the following origin: biliary tract cancer; brain cancer including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

In other embodiments, the chemorepellent is secreted or displayed by a microorganism. By microorganism, it is meant a gram positive or gram negative bacterium, a fungus such as yeast or mold, viruses, whether DNA- or RNA-based.

Identification and Validation of Chemorepellents

Once a potential chemorepellent source has been identified for interrogation or investigation in a chosen migratory cell population, movement of the cell with chemotactic potential is then measured in a high density or high throughput transmigration apparatus. By "high density", it is meant a 96 or 384-well apparatus containing an upper chamber, a polycarbonate or polyester planar membrane and a lower chamber (see Example 9). Briefly, the cell suspension is placed in the upper chamber, on top of the planar membrane and cells induced to migrate by addition of the chemorepellent at varying concentrations to the upper well of the transmigration apparatus (see FIG. 5-6). Following the migration period, the transmigration apparatus is disassembled, a cell lysis and chemiluminescence agent added to the lower (i.e. migration) chamber and the liquid in the lower plate is recovered either by aspiration and delivery into a white 96- or 384-well plate suitable for luminometry or by centrifugation. For centrifugation, the plate of lower chambers fitted with a funnel device for centrifugal transfer of all liquid solutions to a white reading plate suitable for measurement of luminescence. Regardless of which method is used, the white reading plate is shaken orbitally for 10 minutes in the dark, loaded into an automated plate loader and read, well-by-well, in a device suitable for measurement of luminescence. Alternatively, cells in the migration plate may be stained with a fluorescent marker, transferred by aspiration or centrifugation to a black reading plate and the fluorescence read well-by-well in a device suitable for measuring fluorescence. Migration of cells into any well is compared to the migration of cells that have not been exposed to the tested or putative chemorepellent and a repellent index is calculated.

The "Repellent Index" (RI) is a measure of the ability of an agent to induce chemorepulsion of a cell relative to any spontaneous movement of the cell itself. Spontaneous migration is measured without any agent added, while chemokinesis refers to migration in the presence of an agent, where the agent is at equal concentration above, and below, the membrane on which the cells are placed. It is noted that the present apparatus is unable to measure chemokinesis since the device is vertical and the cells detach from the membrane when they squeeze through the membrane pores. As such, cells can't reach an equilibrium and chemokinesis can't be measured.

An agent's repellent index is the ratio of chemorepulsion (CR) to spontaneous migration (SM) induced by the agent, i.e., [(CR)/(SM)]. A "validated chemorepellent" is an agent which exhibits a repellent index equal to or greater than 1.2 over at least a 10-fold change in concentration. For example, in calculating a RI for an agent, migratory responses including chemorepulsion (CR) and spontaneous migration (SM) may be measured over several decades or log scales of concentration. If, over any two consecutive measurements at concentrations which differ by at least 10 fold, the ratio of CR to SM at each of the two contiguous measurements is equal to or greater than 1.2, then the agent is considered a validated chemorepellent.

For studies involving the identification of cells which secrete one or more chemorepellents and the identification of chemorepellents in a solution which may contain one or more chemorepellents, an index has been developed to allow reliable statistical cross-experiment analyses.

The "Migration Index" (MI) is a measure of the ability of a mixture of putative chemorepellent agents, either secretions from cultured mammalian cells or collected fractions therefrom, to induce chemorepulsion of a cell relative to any spontaneous movement the mixture of putative chemorepellent agents might induce in the cell. A mixture's migration index is computed as the ratio of chemorepulsion (CR) observed for the mixture of putative chemorepellent agents relative to the ability of a serum-free medium itself to induce chemorepulsion (i.e., CR is normalized to spontaneous migration (SM)) induced by the incubation medium in which the cells reside) and is represented as [(CR)/(SM)]. As used herein, the term "mixture" when referring to studies involving the conditioned media assay and identification of chemorepellents from a system, includes solutions, cell supernatants, isolates, tissue exudates, non-homogeneous solutions, and fractions, aliquots or subportions thereof.

Agonists and Antagonists of Chemorepellents

Once a chemorepellent is identified, it may be validated using the techniques described above. It is further contemplated that in some situations, using the chemorepellent itself as a therapeutic composition may not be optimal. For example, if a very large protein is identified as a chemorepellent, it would not be feasible to develop that entity as a therapeutic. It would however be advantageous to identify regions, epitopes or fragments of that protein which elicit the migratory response and then to design agonists or antagonists of the chemorepellent agent. These agonists and antagonists may then be employed in pharmaceutical applications or as pharmaceutical compositions which may be administered to a subject to ameliorate, prevent, treat or cure disease indications or conditions associated with, caused by or which have as a component of their etiology the aberrant control or regulation of cell migration. As used herein the term "ameliorate" means to make a situation better or more tolerable.

Identification of the presence of an agent which acts as a chemorepellent, formerly not known to act as such, in certain disease conditions may also serve as a marker or in diagnostic applications. Consequently, the present invention embraces the screening of tissues, cells and biological samples for the secretion, expression or presentation of agents which act as chemorepellents.

Chemorepellent agents identified may be polypeptides, nucleic acid based, may be modified with any posttranslational moieties including but not limited to carbohydrates, lipids and the like. Agonists and antagonists do not have to be of the same type of molecule as the identified or validated chemorepellent. For example, an antagonist of a polypeptide may be a small molecule, antibody, aptamer, adnectin, or any agent which antagonizes the chemorepellent activity of the agent identified.

Chemorepellent agents may be hybrid molecules such as glycoproteins, peptidoglycans, or protein-nucleic acid conjugates. They may be modified by conjugation of delivery moieties, stabilizing moieties or any other moiety which improves or facilitates the pharmaceutical or diagnostic properties of the composition.

The present invention also makes it possible to isolate proteins, lipids or carbohydrates that bind the chemorepellent, including cell surface receptors. The proteins, carbohydrates and lipids that bind the chemorepellent can be used, for example, in screening assays to detect the presence, or absence, of the repellent in cell- or medium-derived mixtures. The binding proteins, carbohydrates or lipids can also be used to block the effect of the isolated chemorepellent.

The invention therefore embraces any binding agent, which can, for example, be an antibody or fragment thereof which has the ability to selectively bind the chemorepellent.

Therapeutic Opportunities
Inflammation

It is believed that by controlling migratory cell movement, one can prevent or reduce the inflammatory response in situations such as bacterial infection, tissue injury-induced inflammation (ischemia-reperfusion injury), crystal-induced inflammation, complement-induced inflammation and oxidative stress (hemodialysis), immune complex-induced inflammation (antibody-mediated glomerunephritis), cytokine-induced inflammation (rheumatoid arthritis), anti-neutrophil cytoplasmic antibodies and vasculitis (autoimmunity against neutrophil components), genetic disorders of neutrophil regulations (hereditary periodic fever syndromes), implant related inflammation, and cystic fibrosis.

In another embodiment, the invention provides a method for inhibiting migration of immune cells to a site of inflammation. "Inflammation" refers to a localized protective response elicited by a foreign (non-self) antigen and/or by injury or destruction of tissue(s), which serves to destroy the foreign antigen, the injurious agent and/or the injured tissue. An "inflammatory response" is that response by the human body to an inflammatory insult. As used herein, an "inflammatory insult" is any event which triggers inflammation. Inflammation occurs when tissues are injured by viruses, bacteria, trauma, chemicals, heat, cold or any other harmful stimulus. In such instances, immune cells such as T cells, B cells or macrophages interface with cells and soluble products that mediate the inflammatory response (e.g. neutrophils, basophils, eosinophils, kinin and coagulation systems and complement cascades).

Inflammation may also be caused by a self-antigen and the subject in need of treatment has an autoimmune disease. "Autoimmune disease" results when a subject's immune system attacks its own organs or tissues, producing a clinical condition associated with the destruction of that tissue, exemplified by diseases such as rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, multiple sclerosis, systemic lupus erythrematosus, etc. As used herein an "immune response" means a physiological response in humans and higher animals to defend the body against the introduction of foreign material Inhibition of immune cell migration to a select site or area of inflammation in any of the foregoing conditions is beneficial, for it inhibits the escalation of the inflammatory response, protecting the specific site involved from 'self damage'.

Cancer

According to another aspect of the invention, a method of inhibiting endothelial cell migration to a tumor site in a subject is provided. The method involves locally administering to or contacting an area surrounding a tumor site in need of such treatment a validated chemorepellent in an amount effective to inhibit endothelial cell migration into the tumor site in the subject. Validated chemorepellent antagonists may also be administered to or be contacted with the tumor site or location. In certain embodiments, the area surrounding the tumor site is not immediate to the tumor site.

According to one aspect of the invention, a method of inhibiting tumor cell metastasis in a subject is provided. The method involves contacting or administering, either locally or systemically, to a tumor site in a subject in need of such treatment a validated chemorepellent, mimic, agonist or antagonist agent in an amount effective to inhibit metastasis of tumor cells from the tumor site in the subject.

Immunodeficiency

According to yet another aspect of the invention, a method of enhancing an immune response in a subject having a condition that involves a selected site is provided. The method involves administering, either locally or systemically or contacting a selected site in a subject in need of such a treatment a chemorepellent antagonist in an amount effective to inhibit immune cell-specific chemorepulsion in the subject.

Contraception/Infertility/Premature Labor

According to another aspect of the invention, a method of contraception is described. The method involves administering an antagonist of a validated chemorepellent in an amount effective to inhibit migration of germ cells in the subject.

According to another aspect of the invention, a method of treating infertility and premature labor is provided. The method involves administering a validated chemorepellent in an amount effective to inhibit immune cells from migrating close to a germ cell in the subject. In further embodiments, the administration is local to a germ cell-containing site of the subject.

Material Surfaces

In one embodiment, any of the agents, compounds or pharmaceutical compositions of the present invention may be used for the treatment of conditions characterized by a need to modulate the direction of cell migration to or from specific sites, locations, tissues, organs, organ transplants or grafts in a subject or patient.

In one embodiment, the compositions of the present invention may also direct, trigger, induce or elicit the movement of cells away from a non-biologic such as a transplant, implant, area or site of microbial infiltration, or device not of biologic origin (material surface) such as those used in orthopedic applications like pins, screws and the like or those used for example in cardiovascular applications such as pacemakers, valves, stents, and the like or dental appliances. In this aspect, the validated chemorepellent or a mimic or agonist coats the material surface with an amount effective to repel immune cells. In addition to the chemorepellent, the material could be coated with a cell-growth potentiating agent, an anti-infective agent and/or an anti-inflammatory agent.

It will be appreciated by one of skill in the art that the compositions and methods of the present invention will be useful in any situation where it is desired to prevent, reduce or eliminate the aggregation of cells, cellular secretions or infiltrates which may interfere with normal body function or healing. By employing the knowledge gained from the present invention, it will be possible to modulate the chemorepulsion of cells by employing antagonists of such chemorepellents, thereby allowing the movement of cells to progress where they otherwise would have been repelled.

It is a preferred embodiment of the present invention to trigger, induce or elicit the chemorepulsive movement of immune cells or cells of immune origins using the chemorepellents identified and/or validated by the methods disclosed herein.

In a specific embodiment, the present invention provides cardiovascular stents coated, impregnated or infused with one or more validated chemorepellents. Such a coated stent can result in high cellular uptake of the drug and thus low viability of vascular smooth muscle cells (VSMC), thus attaining better effects in preventing restenosis compared to cardiovascular stents of the prior art.

Pharmaceutical Compositions

According to another aspect of the invention, a method of inhibiting migration of immune cells to a selected site in a subject is provided. The method involves administering, either locally or systemically, to a selected site in a subject in need of such a treatment a chemorepulsive agent in an amount effective to elicit, trigger, enhance, induce chemorepulsion of immune cells from the site. As used herein "chemorepulsive agents" include chemorepellents, validated chemorepellents, mimics of chemorepellents or validated chemorepellents, and agonists of chemorepellents, and the like.

Alternatively, an agonist of the chemorepellent may be administered for increased effect. Such agonists may be preferred over the chemorepellent because of certain pharmacokinetic or pharmacodynamic properties.

In one embodiment, the chemorepellent effective dose may be calculated based on binding constants. It is expected that the agents of the present invention would exhibit binding constants of between 1-10 nM, preferably between 3-7 nM and more preferably between 4-5 nM for a target. Binding constants may further be approximately 5 nM for the target.

In certain embodiments, the chemorepellents and pharmaceutical compositions comprising chemorepellents may be co-administered with a second agent (e.g., another chemorepellent or with any drug or agent which is not itself a chemorepellent). The co-administered agents may act cooperatively, additively, or synergistically. Co-administered agents, compounds, chemorepellents or therapeutics need not be administered at exactly the same time. According to certain embodiments, a chemorepellent agent is administered substantially simultaneously. By "substantially simultaneously," it is meant that the chemorepellent agent is administered before, at the same time, and/or after the administration of the second agent.

Chemorepellent agents, their antagonists or agonists, and pharmaceutical compositions thereof may be co-administered with any second agent including anti-inflammatory agents, anti-cancer agents, anti-infective agents, immune therapeutics (immunosuppressants) or any therapeutic compound.

An anti-infective agent is an agent which reduces the activity of or kills a microorganism and includes: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter: Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

Anti-cancer agents include Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexatc; Eflorithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatini; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur, Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporlin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate Virlrosidine Sulfate; Vinzolidine Sulfate; Vorozole; Zeniplatin; Zinostatin; Zorubicin Hydrochloride.

Immunosuppressants include Azathioprine; Azathioprine Sodium; Cyclosporine; Daltroban; Gusperimus Trihydrochloride; Sirolimus; Tacrolimus.

Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

As used herein, a subject is an animal. Animals include, but are not limited to, all primates (human and non-human), cows, horses, pigs, sheep goats, dogs, cats, and any other animal which may benefit in any way from receiving as a treatment or therapy the compounds, agents or compositions of the present invention. A subject may also be a patient in need of treatment or prophylaxis.

Identification of Unimodal Fugetaxins

In one embodiment, the present invention provides a method for the control of the movement of such cells by contacting these cells with unimodal fugetactic ligands or unimodal fugetaxins, their agonists or antagonists. In one embodiment the unimodal fugetaxin is galectin-3.

As used herein, a "fugetaxin" is an agent which elicits fugetaxis in a cell or group of cells. "Fugetaxis" is defined as the active movement of a cell away from a chemokinetic agent. A "chemokinetic agent" being any agent or stimulus which elicits, triggers or causes the movement of cells in any direction. In this sense, a fugetaxin is analogous to (i.e., the same as) a chemorepellent. A "unimodal fugetaxin" is a compound which (1) elicits a fugetactic response which is comparable to or greater than the chemotactic (chemoattractant) response elicited by the compound at any given dose; and (2) where the fugetactic response elicited by the compound exceeds the chemotactic response elicited by the compound at a fugetactic effective dose. A "fugetactic effective dose" is that dose of a fugetaxin which causes, induces or triggers the movement of a cell away from the fugetaxin.

These unimodal fugetaxins and methods of the present invention may be developed to treat such as inflammation and diseases or conditions associated with autoimmune responses and various cancers.

The compounds and methods of the present invention may also be used to treat various cancers by controlling leukocytes and acting as novel types of chemorepellent molecules (i.e., unimodal fugetaxins) in various cell types.

In one embodiment of the invention, the fugetactic response elicited by the unimodal fugetaxin occurs with rapid onset. As used herein "rapid-onset" is defined as the production of a measurable fugetactic or chemotactic response within or at approximately one hour after treatment. For certain cell types, rapid-onset may occur at 2, 3, or 4 hours but always by five hours post treatment.

In one embodiment the fugetactic effective dose is at least 10 uM. In a further embodiment the migratory cell is a neutrophil. It is contemplated that the fugetactic effective dose may occur at least within the ranges of 0.01 uM-0.1 uM, 0.1 uM-15 uM, 1 uM-15 uM, 2 uM-10 uM, 5 uM-8 uM or preferably less than 0.1 uM.

According to another aspect of the invention, a method of altering the migration of immune, inflammatory or cancerous cells is provided. The method involves administering or contacting a subject in need of such treatment with a unimodal fugetaxin at a fugetactic effective dose to alter the migration of immune, inflammatory or cancer cells in the subject. Administration, according to the invention, may be by any route, local, systemic or oral.

Alternatively, the migration of immune, inflammatory or cancerous cells may be altered by providing to a subject or contacting a subject in need of such treatment with an antagonist of a unimodal fugetaxin. In this embodiment, the activity of the unimodal fugetaxin would be attenuated and thereby inhibit the fugetaxis of the immune, inflammatory or cancer cell. In one embodiment, the unimodal fugetaxin antagonist is a galectin-3 antagonist.

According to the present invention, unimodal fugetaxin antagonists may comprise small molecules, antisense compounds of either RNA or DNA, siRNA, miRNA, aptamers, antibodies, peptides or peptide fragments, any of which act to interfere, abrogate, attenuate, alter or otherwise inhibit the activity of the unimodal fugetaxin on an immune, inflammatory or cancer cell.

In another embodiment, the method further comprises co-administering with a unimodal fugetaxin, a fugetactic agent, a non-fugetactic agent or other therapeutic compound to the subject. In one embodiment, the fugetactic agent may be stromal derived factor-1 (sdf-1); the non-fugetactic agent may include anti-inflammatory agents and/or an immunosuppressants and the other therapeutic compound may include any drug or moiety previously identified to have therapeutic benefit.

In one embodiment, the subject has an autoimmune disease. In one embodiment the subject has an inflammatory disease or condition. In one embodiment the subject has a hyperproliferative condition. In one embodiment the hyperproliferative condition comprises cancer.

It is to be understood that none of the headings used herein are meant to be construed as limiting, in any manner, any embodiment of the present invention.

EXAMPLES

Example 1

Trans-Well Migration Assay Protocol

Prior to beginning the assay 0.5% Fetal Calf Serum (FCS) in Iscove's Modified Dulbecco's Medium (IMDM) is prepared and stored on ice (Assay Medium). Migratory cells at a concentration of $2 \times 10^7$ cells/ml are suspended in Assay Medium. T-cells isolated from donor blood or buffy coats are allowed to rest overnight in Assay Medium at 37° C. in 5% $CO_2$. Neutrophils, monocytes and B cells are utilized as soon as they are purified from donor blood or other source of human origin. Four serial (10×) dilutions of the ligand are then prepared in Assay Medium (normally 10 μg/ml to 0.01 μg/ml).

The assay plates, Neuroprobe ChemoTx (part number 106-5; 5 μm pore size), are used for leukocytes or granulocytes. For cultured cell lines (Jurkat, Molt4, HL-60 and SupT-1 etc.), part number 106-8 (8 μm pore size) is used. For neutrophils, part number 106-3 (3 μm pore size) is used.

Plates are removed from the packaging, leaving the membrane behind and intact. The membrane is set aside. Into each well is pipetted 31 μl of solution. For media controls and fugetaxis (chemorepellent) samples, Assay Medium is used. For chemoattraction samples, the appropriate dilution of agent in assay medium is used.

Using a sterile needle, all small bubbles present in each well are popped and the membrane is carefully placed onto the plate, starting at one side and slowly lowering the other edge onto the plate.

Then 29 μl is pipetted into each circle imprinted on the polycarbonate or polyester membrane. For media controls and chemoattraction samples, Assay Medium is used. For fugetaxis (chemorepellent) samples, the appropriate dilution of ligand in assay medium is used.

To each 29 uL aliquot above is added 2 µl of cells (40,000 cells). It is important to ensure that before beginning the cells are well suspended and that they are mixed. This mixing can be accomplished by agitating the tube between each addition.

The plate is then covered with the supplied lid and incubated 1-3 hours in a humidified incubator at 37° C. in 5% $CO_2$. Following the incubation period, the liquid from the top of the plate is removed with a tissue or similar blotting material (e.g. a Kimwipe). The membrane is carefully removed from the top of the plate and discarded. Using a multichannel pipettor set at 30 µl, the contents of the wells are transferred to a white microplate (Perkin-Elmer Cultur-Plate 96 #6005689). Using a multichannel pipettor, each well of the microplate is rinsed with 25 µl Phosphate Buffered Saline (Mediatech #21-040-CV) and transferred to the same wells in the white microplate. Using a multichannel pipettor, 50 µl CellTiter-Glo Luminescent Cell Viability Assay (Promega #G7572) is added to each well and mixed.

The plate is read using the Perkin Elmer Victor$^3$V plate reader using the Large Aperture Luminescence setting at 8 mm height above the plate with a dwell time of 1 s to quantify the number of migrated cells.

Example 2

Phenotypic Screening Protocol

For suspension cells, an initial cell count is performed to determine concentration of cells in each flask. The total number of cells required is at least 120×10$^6$. The cells are pelleted (500×g, 10 mins) and resuspended and combined to one 50 ml falcon tube in hybridoma serum free (HSF) media (Gibco 12045). Cells are then washed two additional times with HSF media by centrifuging and resuspending. After the last wash, cells are again pelleted and resuspended in hybridoma serum free (HSF) media supplemented with Penicillin-Streptomycin (ATCC 30-2300, 1%-final concentration 100 units/ml-100 µg/ml, HSF+PS) to a concentration of 3×10$^6$/ml based on the original cell count. 5 ml (15×10$^6$ cells) is transferred to each of eight 25 cm$^2$ flasks already containing 10 ml HSF+PS.

Adherent cells are grown to approximately 70~90% confluence in 8-75 cm$^2$ flasks. The cells are rinsed two times with approximately 10 ml of HSF+PS and covered with 30 ml HSF+PS.

The flasks are incubated at 37° C., 5% $CO_2$, and the culture supernatant of the flask harvested at varying time periods (one hour after placing back in the incubator (Day 0), 24 h, 48 h, 72 h, etc up to 7 days). To harvest, the culture fluid should be centrifuged at 500×g for 10 minutes and then filtered to a new tube using 0.2 µm Costar syringe filters (Catalog #8110). Storage of multiple aliquots of 250 µl each can be in microcentrifuge tubes. The remaining supernatant can be stored in a falcon tube. All samples are stored at −80° C.

After all supernatants have been collected, they are used as ligand samples in the transmigration assay at 100%, 10%, and 1% strength. A positive control (which can be stromal derived factor −1 (SDF-1) (0.1, 1, and 10 µg/ml) and a HSF+PS negative control should also be run in the assay.

Example 3

Quantitation of the Migratory Response of Human Primary Neutrophils, CD4+ Lymphocytes and CD8+ Lymphocytes to Galectin-3

It has been discovered that Galectin-3 is a unimodal fugetaxin that can be titrated to control cellular behavior. Each of galectin-1,2,3,5,7 and 8 was tested in a 96 trans-well migration assay for their effects on neutrophils, CD4+ and CD8+ T lymphocytes. The full-length galectin protein molecules were purchased from different vendors (Sigma, R&D and BioVision).

The assay was performed according to the methods described herein but with the following modifications to eliminate noise and increase the signal to noise ratio.

First, fresh human peripheral blood was drawn less than 5 minutes before the start of purification. Neutrophils were isolated using 5 ml Polymorph prep (Axis Shield, Netherlands) per 5 ml fresh blood layered on top in a 15 ml conical tube. Blood was then centrifuged 600×g for 60 minutes. The lower band containing neutrophils was then extracted using a Pasteur pipette. Cells were mixed 1:1 with 0.45% NaCl and centrifuged at 500×g for 10 minutes. Supernatant was removed and cells washed with 50 ml 1% Penicillin-Streptomycin IMDM (ATCC, Manassas, Va.) and spun at 500×g for 10 minutes. Supernatant was removed and pellet washed with 10 ml 0.5% FCS, 1% Penicillin-Streptomycin IMDM. Cells were counted and then resuspended in the appropriate volume. The assay was carried out for one to one-and-one-half hours at 37° C. with 5% $CO_2$.

Figure 1B:
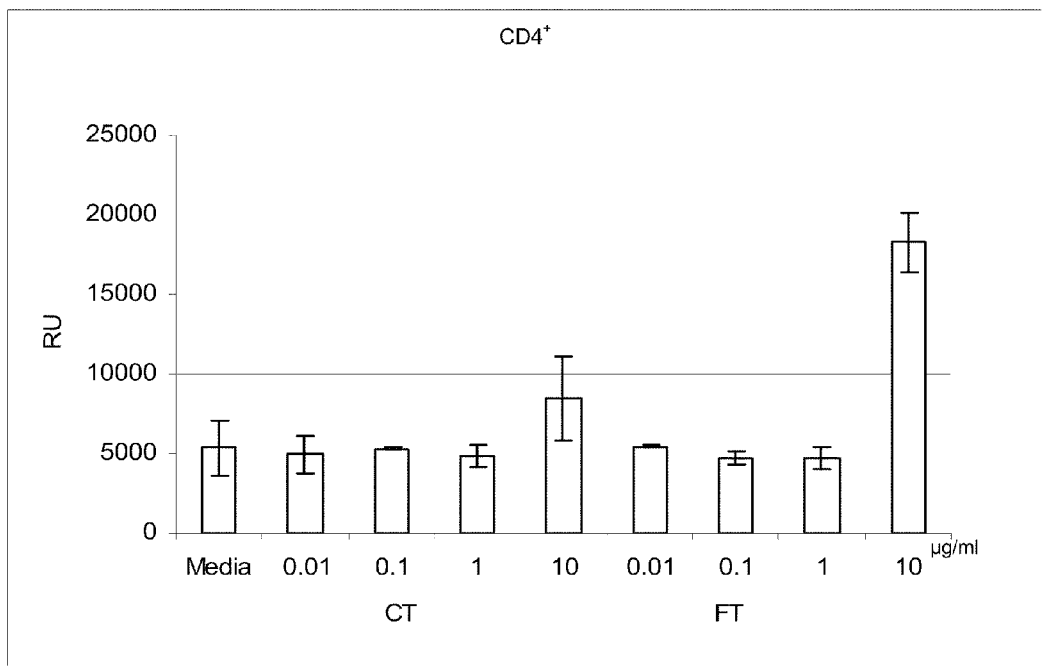
Figure 1C:
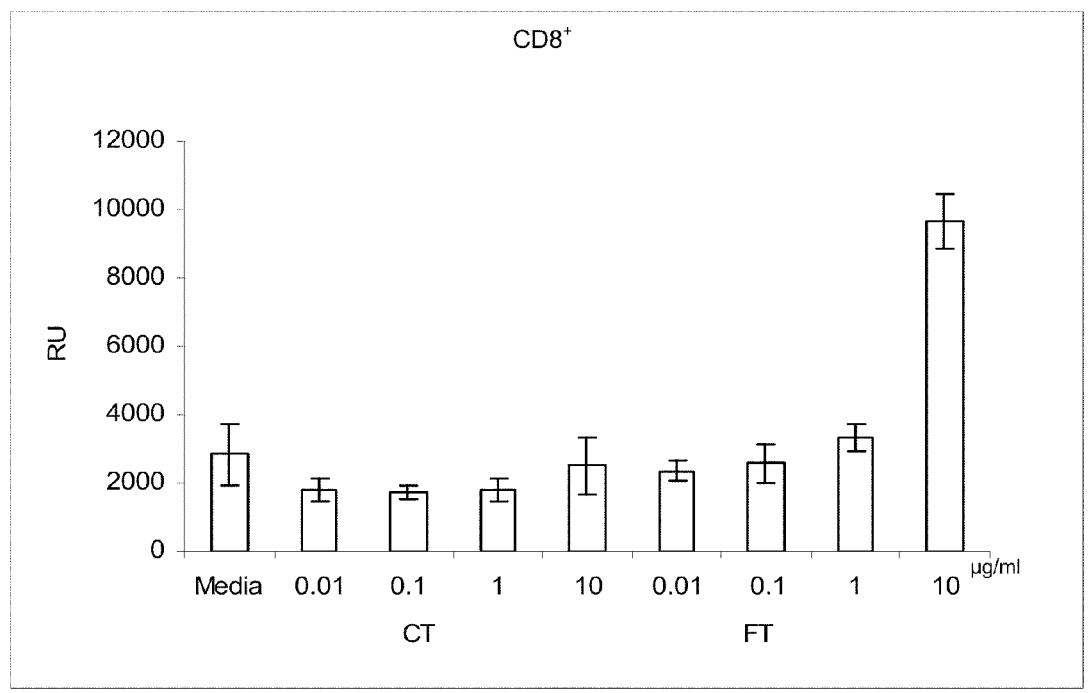

FIG. 1 shows the results of the study of Galectin-3. RU are luminescence units from a CellTiter-Glo (Promega, Madison, Wis.) assay of cells that have migrated through a polycarbonate membrane with a 5 µm pore size to the lower portion of a transwell (Neuro Probe, Gaithersburg, Md.). Human primary neutrophils (A), CD4$^+$ lymphocytes (B), or CD8$^+$ lymphocytes (C) were added to the upper chamber. In the case of fugetaxis (chemorepulsion) (FT, right side of each graph), the upper chamber also contained galectin-3 in the indicated concentrations while the lower chamber contained media. For chemotaxis (chemoattraction) (CT, left side of each graph), the upper chamber contained media and the lower the indicated concentrations of galectin-3. The media control contained only media in both chambers.

The data represent the measurements taken at 1 hour. It is shown in the figure that galectin-3 is fugetactic (chemorepulsive) in the assay at a dose of 10 µg/ml. It was determined and can be seen in the figure that micromolar concentrations of this molecule can induce the movement of several cell types (Neutrophils, CD4+ and CD8+ T lymphocytes) in a predominantly unidirectional manner. In all three cell types, 2 to 3 fold more cells are repelled by 10 µg/ml galectin-3 than are attracted by it over the same time period. To applicant's knowledge, this effect has never been documented.

Figure 3:
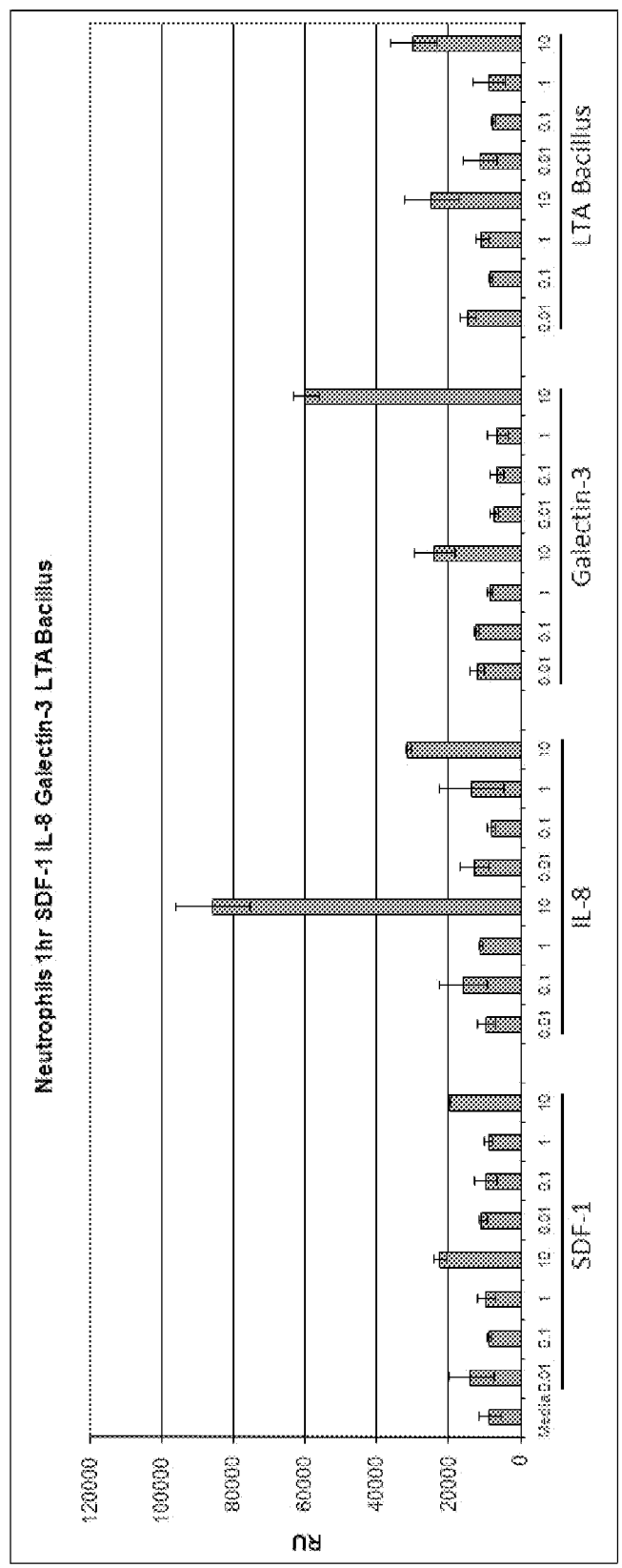
FIG. 3 is a bar graph comparing chemotactic response of neutrophils to varying concentrations (in μg/ml) of SDF-1, IL-8, galectin-3, and LTA from *Bacillus subtilis*. The first four bars for each agent indicate positive chemotaxis while the second four indicate negative chemotaxis.
Figure 4:
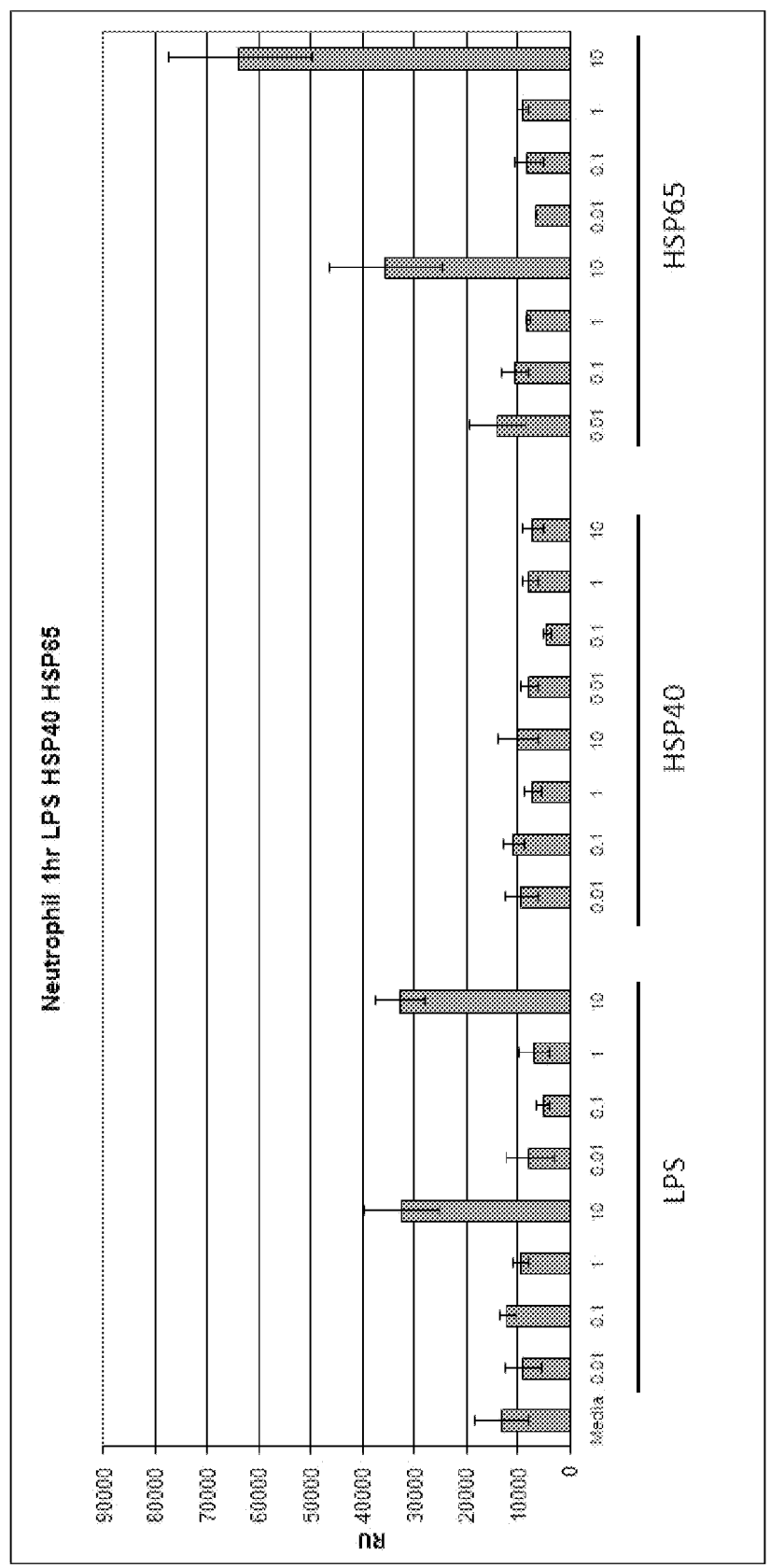
FIG. 4 is a bar graph comparing positive and negative chemotactic response of neutrophils to varying concentrations (in μg/ml) of LPS, HSP-40, and HSP-65. The first four bars for each agent indicate positive chemotaxis while the second four indicate negative chemotaxis.

In comparison studies performed by the assay methods described herein and illustrated in FIGS. 3 and 4, neutrophils were investigated for their response at 1 hour to other ligands.

It is shown in FIG. 3 that at 10 uM, neutrophils acted identically in their chemotactic (chemoattractant) and fugetactic (chemorepellent) responses to stromal derived factor-1(sdf-1) and lipoteichoic acid (LTA). Neutrophils were also over twice as chemotactic (chemoattractant) as fugetactic (chemorepellent) in response to interleukin-8 (IL8).

In FIG. 4 it is shown that neutrophils were almost three times as fugetactic (chemorepellent) as chemotactic (chemoattractant) in response to galectin-3 and were almost twice as fugetactic (chemorepellent) as chemotactic (chemoattractant) in response to heat shock protein 65 (HSP65). It is also shown in FIG. 4 that at 10 uM, neutrophils acted identically in their chemotactic (chemoattractant) and fugetactic (chemorepellent) responses to lipopolysacharide (LPS).

Example 4

Figure 2A:
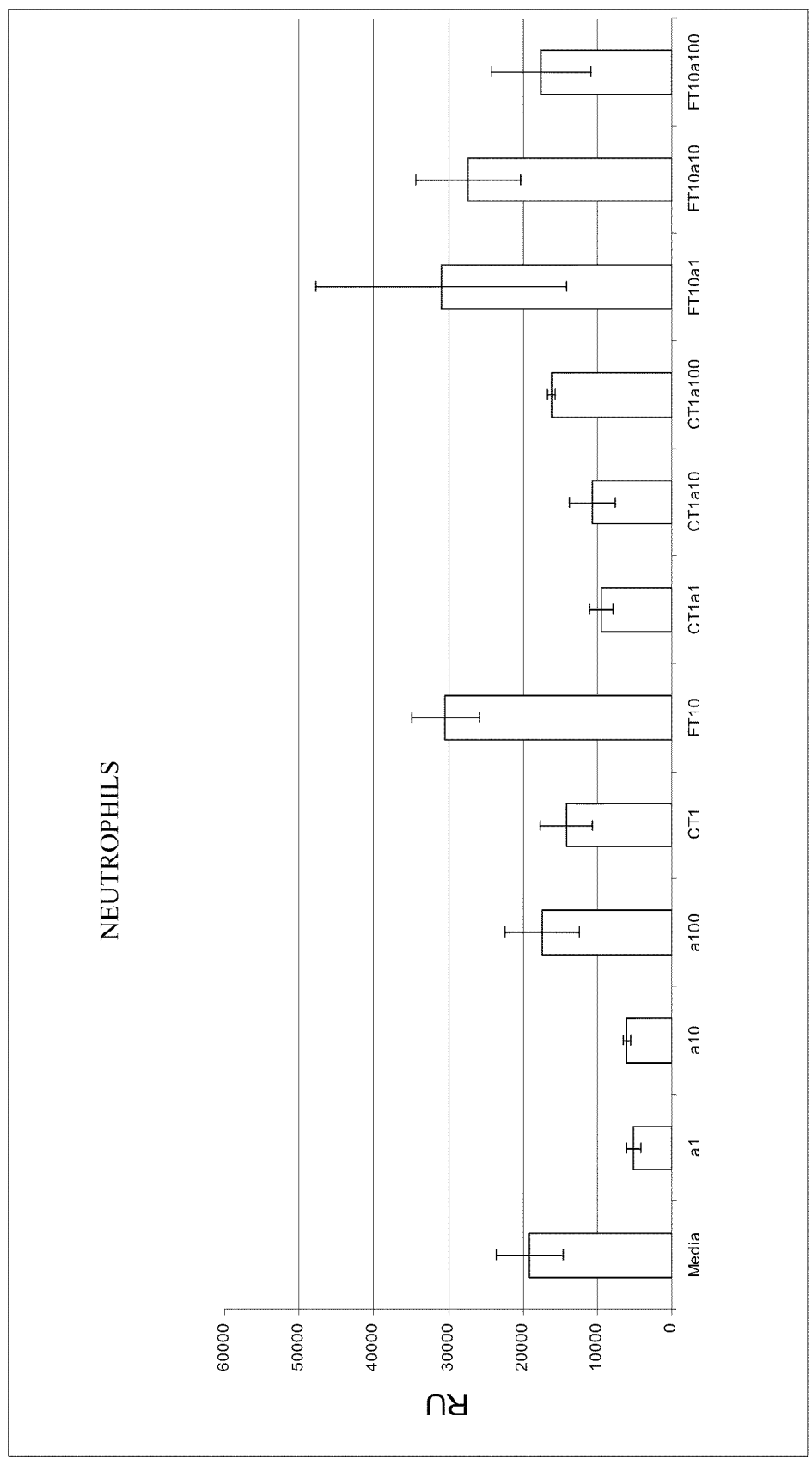
FIGS. 2A-C are bar graphs showing the inhibition of chemotactic response of neutrophils and lymphocytes to galectin-3 using galectin-3 antibody.
Figure 2B:
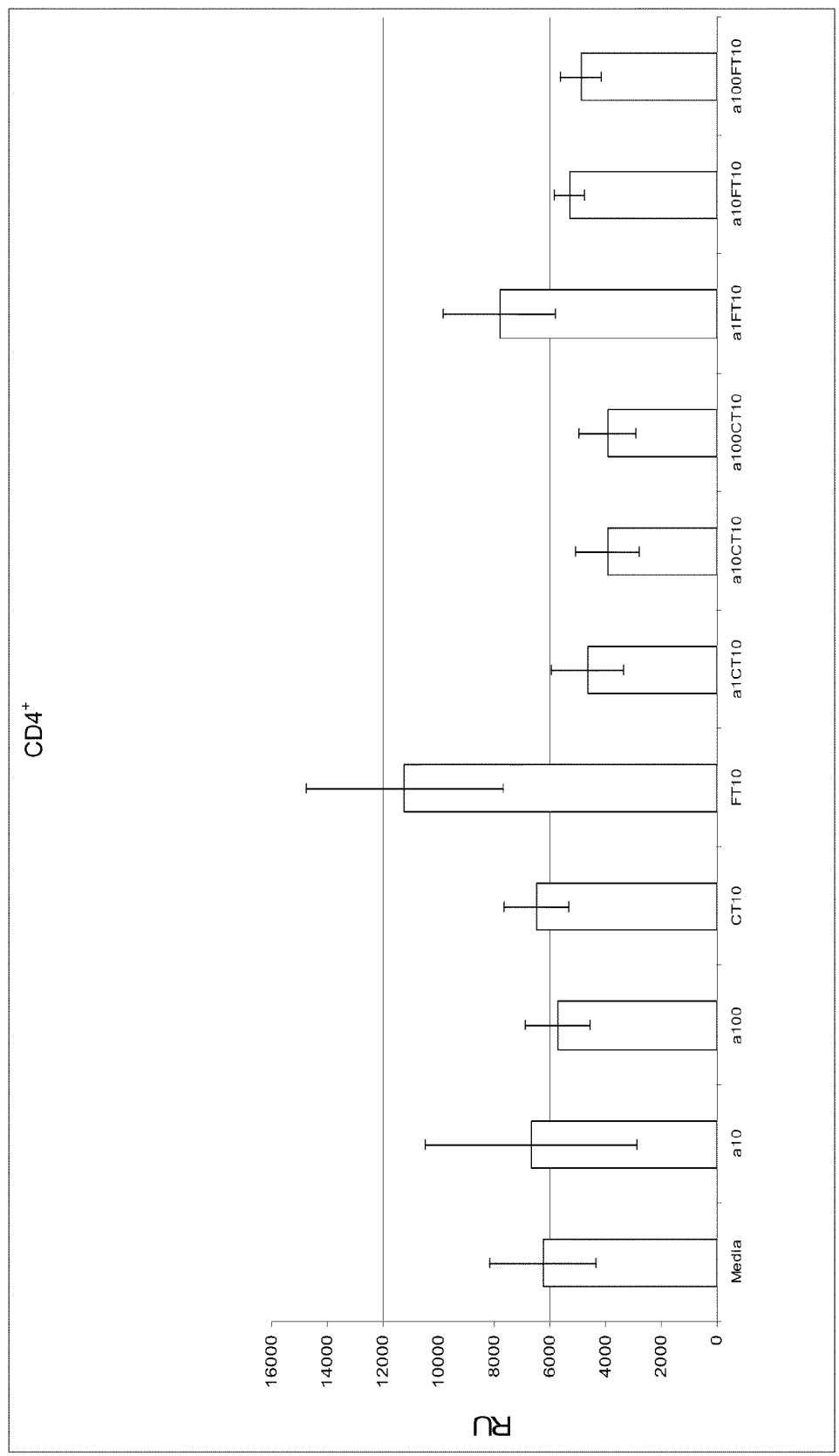
Figure 2C:
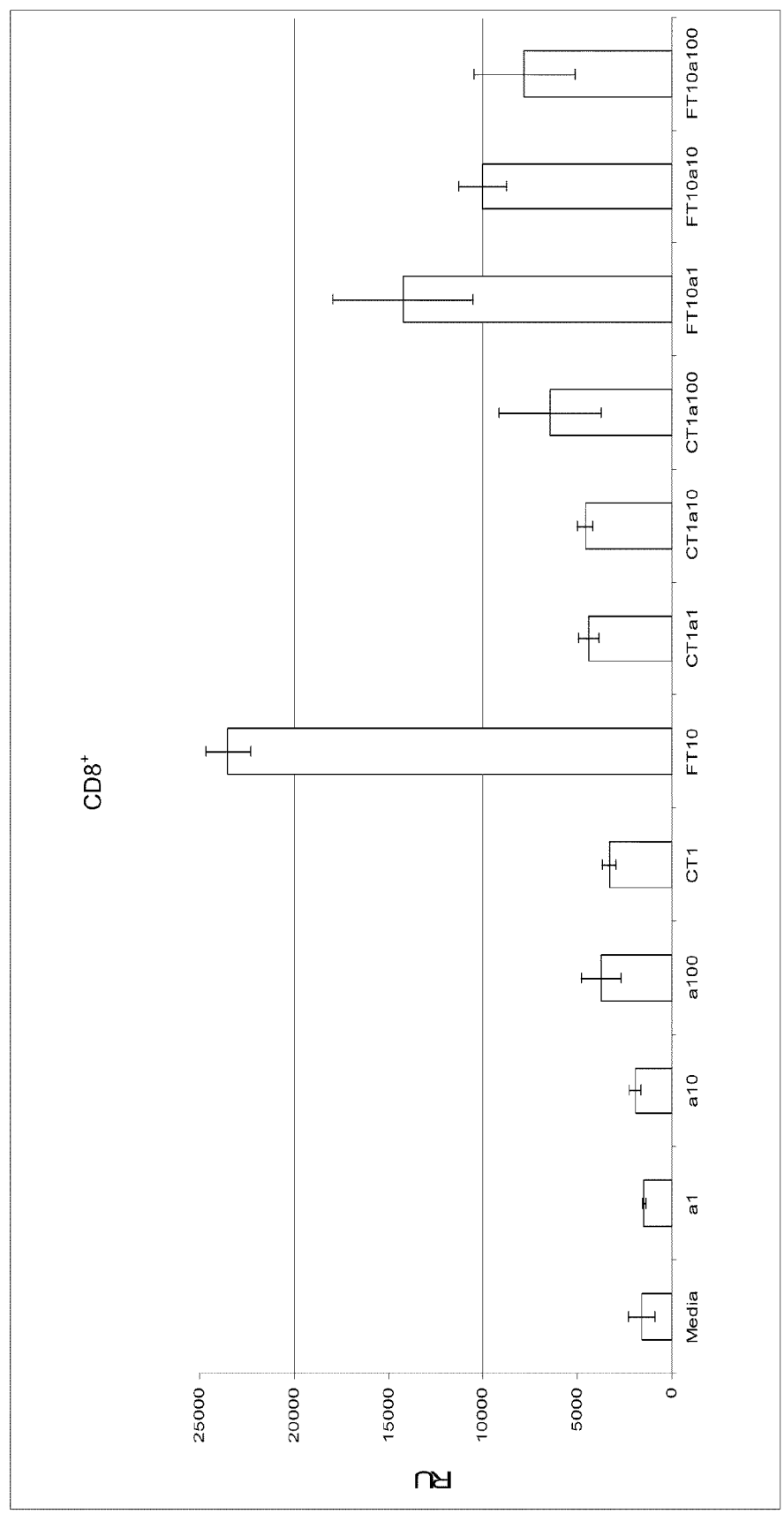

Confirmation of Migratory Response of Human Primary Neutrophils, CD4+ Lymphocytes and CD8+ Lymphocytes to Galectin-3: Antibody Study The results of the antibody inhibition assay are shown in FIG. 2. In the figure, RU are luminescence units from a CellTiter-Glo (Promega, Madison, Wis.) assay of cells that have migrated through a polycarbonate membrane with a 5 μm pore size to the lower portion of a transwell (Neuro Probe, Gaithersburg, Md.). Human primary neutrophils (A), CD4+ lymphocytes (B), or CD8+ lymphocytes (C) were added to the upper chamber. The media control contained only media in both chambers. For samples a1 through a100, both the top and bottom chambers of the well contained a monoclonal antibody to galectin-3 (BD Biosciences, San Jose, Calif.) at 1, 10, or 100 μg/ml. For CT1 samples, the upper chamber contained only media while the lower chamber contained 1 μg/ml galectin-3. For FT10 samples, the upper chamber contained 10 μg/ml galectin-3 while the lower contained only media. In all samples labeled with a1, a10, or a100, antibody was present in both upper and lower chambers at the indicated concentrations.

The protocol was the same as described above, and the system was challenged with antibody to galectin-3. The Figure shows that the number of migrating cells decreased with increasing concentrations of anti galectin-3 antibody. The data clearly show that the fugetactic (chemorepellent) effect of galectin-3 can be abrogated in a directly competitive manner and supports the mechanism proposed in Example 3. As such, galectin-3 antibodies can act as unimodal fugetaxin antagonists.

Example 5

Response of Human Primary Neutrophils, CD4+ Lymphocytes and CD8+ Lymphocytes to Other Unimodal Fugetaxins Using the methods described in Example 3 above, other compounds and/or ligands were tested for their ability to act as unimodal fugetaxins. Table 1 lists those compounds and their effect on human neutrophils, CD4+ lymphocytes and CD8+ lymphocytes. A "+" in the Table indicates a positive hit as a unimodal fugetaxin, as that term is defined herein, for that particular cell type. No data indicates that the agent did not satisfy the definition of a unimodal fugetaxin.

TABLE 1

| Unimodal Fugetaxins | | | |
|---|---|---|---|
| Ligands | CD4+ | CD8+ | Neutrophils |
| Galectins | | | |
| Galectin-1 | | | |
| Galectin-2 | | | |
| Galectin-3 | + | + | + |
| Galectin-7 | | | |
| Galectin-8 | | | |
| Heat Shock Proteins | | | |
| HSP25 | | | + |
| HSP27 | | | + |
| HSP40 | | | |
| HSP47 | | | |
| HSP60 | + | | + |
| HSP65 | + | | + |
| HSP70 | + | | + |
| HSP90 | + | | + |
| TLR Agonists | | | |
| Pam3CSK4 | + | + | + |
| HKLM | + | | |
| Poly(I:C) | | | |
| E. Coli K12 LPS | + | + | + |
| S. typhimurium Flagellin | + | + | + |
| FLS1 | + | | + |
| Imiquimod | + | | + |
| ssRNA40 | + | + | + |
| ODN2006 | + | + | + |
| Bacterial | | | |
| LTA Staph | | + | + |
| Zymosan A | | | |
| Paclitaxel | | | |
| Lipid A Diphos | | | |
| PGN Staph | | | |
| LTA Bacillus | | | + |
| Lipid A E. coli Monophos | | | |
| muramyl dipeptide | | | |
| LPS | + | + | + |
| Viral Ligands | | | |
| rhMMP-2 | | | |
| rvCMV UL146 | | | |
| rvMIP-I | | | + |
| rvMCV Type II | | | |
| rv IL-10 | | | |
| rwnv NS3 Protease | | | + |
| gp120 | | | |

Example 6

Additional Migration Studies

Additional migratory response studies were performed using the cell type Eo-HL60, which corresponds to a human myeloid leukemia cell line known as HL-60 clone 15. These cells, which have been treated with compounds known to cause their differentiation from a myeloid cell type to an eosinophil-like cell type, were utilized as surrogates for eosinophils due to their relative scarcity.

The experiments with the below cell types and ligands were performed as described in Example 1. The results reported reflect the net observed migratory response of the cells to the ligand and are not based on the definition of unimodal fugetaxins.

HL60 cells (clone 15) were obtained from the American Type Culture Collection (ATCC, Manassas Va.). To maintain and expand the cells in an undifferentiated phenotype, the cells were cultured in RPMI-1640 media supplemented with 10% fetal bovine serum, 100 I.U./ml penicillin, and 100 ug/mL streptomycin in a humidified incubator at 37° C. with 5% $CO_2$. To induce their differentiation to an eosinophil-like phenotype (Eo-HL60), cells were transferred to new flasks utilizing the above culture conditions, but supplemented with 0.5 mM n-butyric acid and 5 ng/ml GM-CSF and incubated for 7 days prior to assay. The data are summarized in Table 2.

TABLE 2

Migratory response in cells

| Agent | Cell Type | Migratory Response |
|---|---|---|
| Galectin-1 | Monocyte | chemorepulsion |
| Galectin-3 | Monocyte | chemorepulsion |
| HSP27 Human | Monocyte | chemorepulsion |
| HSP40 Human | Monocyte | chemorepulsion |
| Poly(I:C) | Monocyte | chemorepulsion |
| S. typhimurium Flagellin | Monocyte | chemorepulsion |
| Imiquimod | Monocyte | chemorepulsion |
| Paclitaxel | Monocyte | chemorepulsion |
| N-acetylmuramyl | Monocyte | chemorepulsion |
| Cathespin G, Human Neutrophil | Monocyte | chemorepulsion |
| Dexamethasone | Monocyte | chemorepulsion |
| Glucan (from Baker's Yeast) | Monocyte | chemorepulsion |
| Concanavalin A | Monocyte | chemorepulsion |
| Hyperforin | Monocyte | chemorepulsion |
| MIP-1 beta | Monocyte | chemorepulsion |
| RANTES | Monocyte | chemorepulsion |
| MCP-4 | Monocyte | chemorepulsion |
| SLC | Monocyte | chemorepulsion |
| Eotaxin-2 | Monocyte | chemorepulsion |
| Eotaxin-3 | Monocyte | chemorepulsion |
| Fractalkine | Monocyte | chemorepulsion |
| Galectin-7 | B-cell | chemorepulsion |
| Poly(I:C) TLR3 | B-cell | chemorepulsion |
| Zymosan A (S. cerevisiae cell wall) | B-cell | chemorepulsion |
| Lipomannan M. smegmatis | B-cell | chemorepulsion |
| Purified LTA from S. aureus | B-cell | chemorepulsion |
| Standard LTA from S. aureus | B-cell | chemorepulsion |
| rvMIP-I | B-cell | chemorepulsion |
| Troponin I, From Heart | B-cell | chemorepulsion |
| Cathespin G, Human Neutrophil | B-cell | chemorepulsion |
| Pectin esterified from K Salts | B-cell | chemorepulsion |
| Concanavalin A | B-cell | chemorepulsion |
| Anthrax Lethal Factor | B-cell | chemorepulsion |
| Genistein | B-cell | chemorepulsion |
| Resveratrol | B-cell | chemorepulsion |
| Quercetin dihydrate | B-cell | chemorepulsion |
| Capsaicin | B-cell | chemorepulsion |
| EGCG ((−)-Epigallocatechin Gallate) | B-cell | chemorepulsion |
| MIP-1 beta | B-cell | chemorepulsion |
| RANTES | B-cell | chemorepulsion |
| Eotaxin | B-cell | chemorepulsion |
| MCP-4 | B-cell | chemorepulsion |
| HCC-1 | B-cell | chemorepulsion |
| Leukotactin-1 | B-cell | chemorepulsion |
| TARC | B-cell | chemorepulsion |
| MDC | B-cell | chemorepulsion |
| Eotaxin-2 | B-cell | chemorepulsion |
| Eotaxin-3 | B-cell | chemorepulsion |
| Fractalkine | B-cell | chemorepulsion |
| Galectin-1 | Eo-HL60 | chemorepulsion |
| Galectin-2 | Eo-HL60 | chemorepulsion |
| HSP27 Human | Eo-HL60 | chemorepulsion |
| HSP32 Rat | Eo-HL60 | chemorepulsion |
| HSP40 Human | Eo-HL60 | chemorepulsion |
| HSP47 Human | Eo-HL60 | chemorepulsion |
| HSP60 Mouse | Eo-HL60 | chemorepulsion |
| HSP70 Human | Eo-HL60 | chemorepulsion |
| HSP90 Human | Eo-HL60 | chemorepulsion |
| Pam3CSK4 | Eo-HL60 | chemorepulsion |
| HKLM (heat killed L. monocytogenes) | Eo-HL60 | chemorepulsion |
| Poly(I:C) | Eo-HL60 | chemorepulsion |
| FLS-1 | Eo-HL60 | chemorepulsion |
| Imiquimod | Eo-HL60 | chemorepulsion |
| Paclitaxel | Eo-HL60 | chemorepulsion |
| Lipid A Diphos | Eo-HL60 | chemorepulsion |
| P. gingavalis LPS | Eo-HL60 | chemorepulsion |
| Lipomannan M. smegmatis | Eo-HL60 | chemorepulsion |
| LTA Staph | Eo-HL60 | chemorepulsion |
| Standard LTA from S. aureus | Eo-HL60 | chemorepulsion |
| N-acetylmuramyl (MDP) | Eo-HL60 | chemorepulsion |
| Cathespin G, Human Neutrophil | Eo-HL60 | chemorepulsion |
| Resveratrol | Eo-HL60 | chemorepulsion |
| Quercetin dihydrate | Eo-HL60 | chemorepulsion |

Example 7

Purification of Polymorphonuclear Cells (PMNs, Primary Human Neutrophils)

To obtain primary human neutrophils, up to 80 ml of blood is drawn from a human donor in sodium heparin Vacutainer tubes (Becton-Dickinson). 5 milliliters (5 ml) of blood is then layered on to 5 ml of Polymorphprep (Axis-Shield) in 15 ml conical centrifuge tubes. After centrifugation for 60 minutes at 600×g in a swinging bucket rotor, the plasma and peripheral blood mononuclear cells (PBMC) are removed and discarded. The second band of cells containing the PMNs is then removed to a 50 ml conical tube using a glass Pasteur pipette. An equal volume of 0.45% NaCl is then added to the PMN to wash. After centrifugation for 10 minutes at 500×g, the supernatant is removed and the PMN pellet resuspended in 50 ml of Iscove's Modified Dubelco's Medium (IMDM) (Cellgro, Herndon, Va.). The PMN are again centrifuged for 10 minutes at 500×g and the supernatant removed. After resuspending in 30 ml IMDM, the number of cells is quantitated using a hemacytometer (Reichert). It is noted that if the original blood volume was less than 30 mL then cells were resuspended in 10 mL to achieve an accurate hemocytometer count. Residual red blood cells contaminating the PMN preparation are then removed by positive selection using glycophorin A microbeads (Miltenyi Biotec, Auburn, Calif.) per the manufacturer's instructions. The resulting PMN are then diluted to 50 ml with IMDM. After centrifugation at 500×g for 10 minutes, the supernatant is removed and the PMN resuspended in 15 ml IMDM supplemented with 0.5% heat inactivated fetal calf serum (FCS) (ATCC, Manassas, Va.). After another centrifugation for 10 minutes at 500×g, the supernatant is again removed and the PMN resuspended in 7 ml 0.5% FCS in IMDM (assay medium) and transferred to a 15 ml conical centrifuge tube. The PMN are then quantitated using a hemacytometer. The concentration of PMN is then adjusted to $2 \times 10^7$ per ml by another centrifugation and removal of the appropriate volume of assay medium prior to transmigration assay of Example 9.

Example 8

Purification of Peripheral Blood Mononucleocytes (PBMCs)

For primary human T cells, up to 80 ml of blood is drawn from a human donor in sodium heparin Vacutainer tubes (Becton-Dickinson). The blood (between 10 and 15 ml per tube) is then layered onto 30 ml of Lymphocyte Separation Medium (LSM) (Cellgro, Herndon, Va.) in a 50 ml conical centrifuge tube and centrifuged for 20 minutes at 2440×g in a swinging bucket rotor. After removing the majority of the plasma from the top of each tube, the peripheral blood mononucleocyte (PBMC) layer is removed and transferred to fresh 50 ml conical centrifuge tubes. The tubes are then filled to 50 ml with IMDM and centrifuged for 10 minutes at 500×g. All but approximately 5 ml of the supernatant is then removed and the pellet resuspended with 25 ml IMDM and the centrifugation repeated. After removal of the supernatant, the cells are resuspended and combined to one 50 ml tube (per subject) and brought to a total volume of 50 ml. The cells are then counted using a hemacytometer (Reichert). After centrifugation under the same conditions, the supernatant is removed and the cells processed using the appropriate Miltenyi Biotec (Auburn, Calif.) negative selection kit to enrich for the desired cell type according to manufacturers instructions. The resulting purified cells are then diluted to 50 ml with IMDM. After centrifugation at 500×g for 10 minutes, the supernatant is removed and the cells resuspended in 15 ml IMDM supplemented with 0.5% heat inactivated fetal calf serum (FCS) (ATCC, Manassas, Va.). After another centrifugation for 10 minutes at 500×g, the supernatant is again removed and the cells resuspended in 7 ml 0.5% FCS in IMDM (assay medium) and transferred to a 15 ml conical centrifuge tube. The cells are then quantitated using a hemacytometer. When enriching for monocytes, the concentration of cells is adjusted to $2 \times 10^7$ per ml by centrifugation and removal of the appropriate volume of assay medium. For all other cell types, the tube cap is replaced with one from a 25 cm$^2$ tissue culture flask (Corning) and the cells stored overnight in a humidified 37° C. incubator with 5% $CO_2$. The concentration of the cells is adjusted as for monocytes just prior to transmigration assay of Example 9.

It is noted that this procedure may be used to isolate and/or purify monocytes. In the monocyte purification method, a further step is included for platelet removal via the use of CD61 microbeads also purchased from Miltenyi Biotec (Auburn, Calif.).

Example 9

High Throughput Transmigration Assay

In the course of assay development for the study of cell migration, it was necessary to be able to quantify the effects of the agents being studied. Efforts to develop methods for this purpose resulted in a high throughput transmigration assay which is improved over the original assay reported in Example 1 in that it affords statistically reproducible measurements of migration and therefore allows for better comparisons across experiments.

Figure 5:
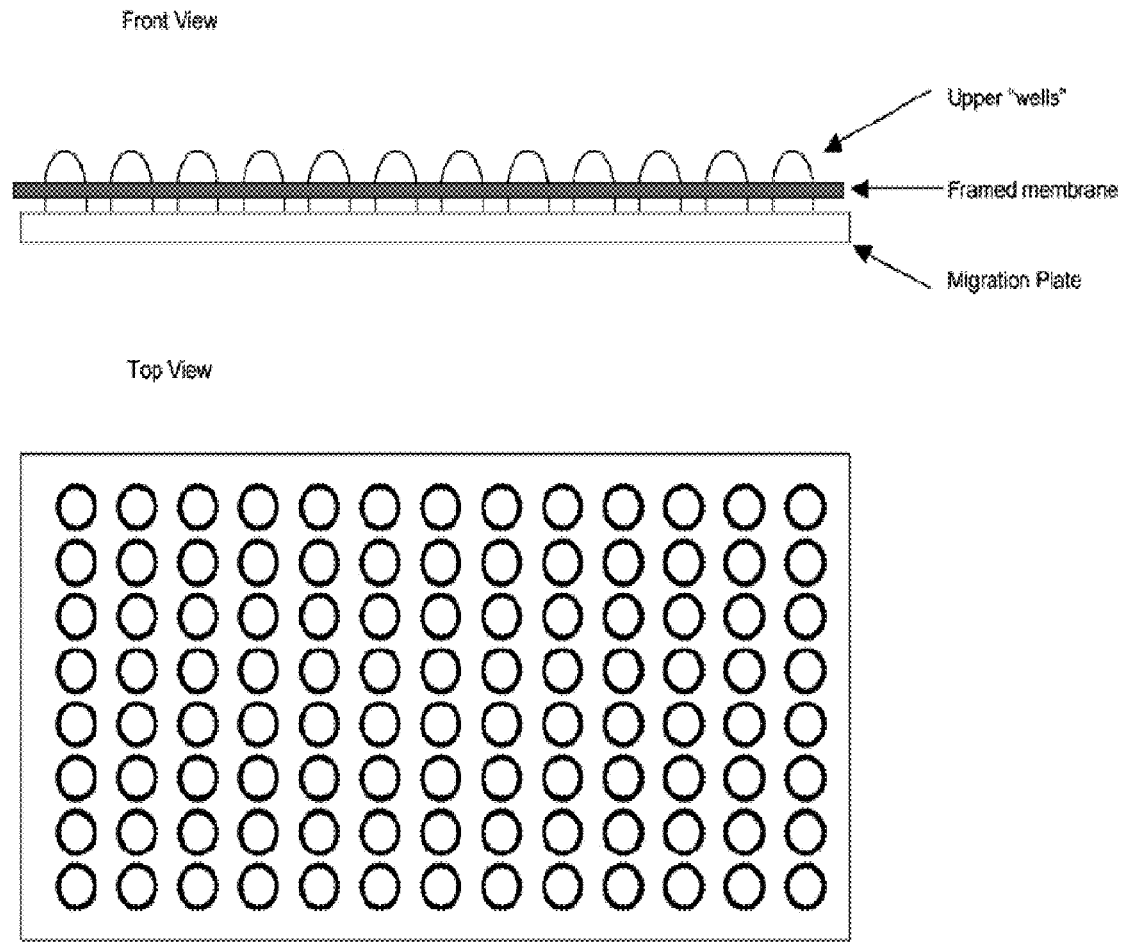
FIG. 5: High throughput screening apparatus for analysis of cell migration.
Figure 6:
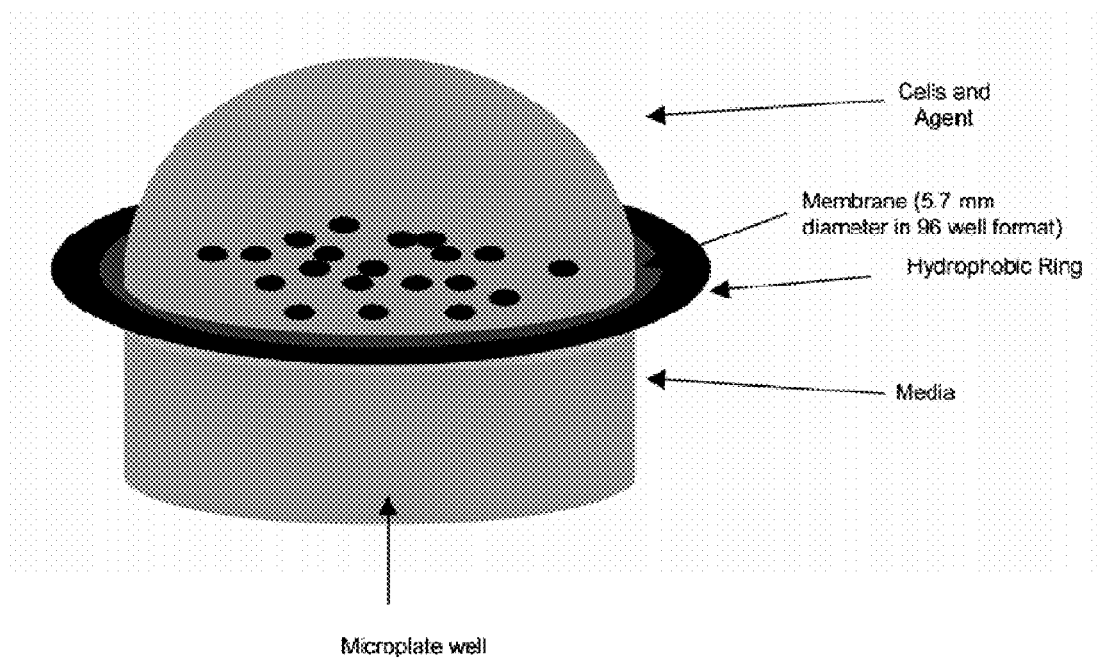
FIG. 6: Well configuration for analysis of negative chemotaxis.

Migration away from a chemical or biological agent (chemorepulsion (CR)) was measured using ChemoTx plates (Neuroprobe). These plates contain a planar polycarbonate or polyester membrane that has been etched and perforated so that cells can move along the etched tracks and fall through perforation holes, enabling the cells to be collected and the number of migrated cells quantified (FIGS. 5-6). Several dilutions (normally 4 in 10-fold increments) are prepared of the agent of interest. For neutrophils, plates with 3 μm pore membranes are used, while for all other primary cell types, 5 μm pore membranes are used. Membranes may, or may not, be coated with polyvinylpyrrolidine (PVP) as a wetting agent.

For spontaneous migration controls and chemorepulsion (CR) assays, 31 μl of assay medium is pipetted into the lower well of the transmigration apparatus (FIGS. 5-6). For spontaneous migration controls and chemoattraction (CA) assays, 29 μl of assay medium is pipetted into upper chamber of the transmigration apparatus (FIG. 5). For CR, the upper well assay medium contains the agent or candidate chemorepellent. For spontaneous migration controls, the upper well assay medium contains only IMDM to which FCS has been added to a final concentration of 0.5% (v/v).

Cells are aliquoted into 200 uL fractions and each kept at 37° C. until ready to plate. This subdivision and preservation of cells at the appropriate temperature allows better consistency across the timecourse of the assay.

For spontaneous migration controls and CR, 2 μl of cell suspension (approximately 40,000 cells) is added to the upper chamber to initiate migration. Migration is allowed to proceed for a specified period of time at 37° C. and 5% $CO_2$. Neutrophil migration occurs for 1 hour, B cells or monocytes migrate for 2 hours and T cells migrate for 3 hours.

After the incubation period, the liquid on top of the membrane is removed by gentle wiping with a KimWipe (Kimberly-Clark), followed by removal of the membrane from the migration (lower) plate. Using a multichannel pipettor, 5 μl of CellTiter-Glo (Promega, city state) is added to each well of the migration plate to quantitate the number of cells present in the well. The contents of each well are then transferred to a 96 well white reading plate suitable for measurement of luminescence (e.g. OptiPlate (Perkin Elmer)) in which 25 μl of phosphate buffered saline (PBS) (Cellgro) has been added. This can be accomplished either by multichannel pipet or by using a funnel plate apparatus (Neuroprobe) in a swinging bucket centrifuge.

The white reading plate is then incubated with orbital shaking in the dark for 10 minutes before reading luminescence in a microplate reader (e.g. Victor3 (Perkin Elmer)). As the luminescent signal was determined to persist without variation for up to 30 minutes, 50 plates can be read in an automated plate loading and plate reading mode using a suitable microplate reader.

The luminescence output correlates directly with the number of migrated cells. The extent of cell migration is computed relative to spontaneous migration for the specific cell type and donor in any given experiment.

Example 10

Preparation of a Conditioned Medium

In other studies, a conditioned medium was employed to identify chemorepellents. In these studies, the conditioned medium was prepared by incubation of cells of mammalian origin in a serum-containing growth medium until the cell culture reached a critical density. Critical density is reached for cells grown in suspension when the cell number exceeds $120 \times 10^6$. For adherent cells, critical density is reached when the cells reach 70-90% confluency. Following growth to critical density, the cells were collected, washed twice in Hybridoma Serum Free Medium (Gibco) supplemented with Penicillin-Streptomycin (ATCC 30-2300, 1%-final concentration 100 units/ml-100 μg/ml) (HSF-PS), transferred to fresh HSF-PS for at least 24 hours and incubated for as long as 360 days. For suspension cells, this washing was accomplished by centrifugation and resuspension in HSF-PS. These suspension cells were seeded at a final density of $1 \times 10^6$ cells per ml in eight 25 cm$^2$ flasks (15 ml each). For adherent cells, 8 flasks were grown to critical density and rinsed with HSF-PS while still adherent to the flask bottoms. When utilizing 75 cm$^2$ flasks, the cells were covered with a final volume of 30 ml HSF-PS, but when using 175 cm$^2$ flasks, 70 ml was used. The flasks were incubated in a humidified 37° C. incubator, 5% $CO_2$, and the culture supernatant of the flask harvested at times varying from 1 hour to 360 days. The process of harvesting culture supernatant at selected timepoints is referred to herein as "timed aliquot selection."

To harvest the supernatant, the culture fluid was centrifuged at 500×g for 10 minutes and then filtered to a new tube using 0.2 µm syringe filters. Alternatively, the supernatants can be filtered using sterile 0.2 µm filter units and the supernatant stored in the included bottles. Storage of multiple aliquots of 250 µl each can be in microcentrifuge tubes. The remaining supernatant can be stored in a conical tube or left in the sterile filter unit receiver flask. All samples were stored at −80° C.

Example 11

Identification and Isolation of Chemorepellents from Conditioned Media

Following growth or maintenance in a conditioned media as described in Example 10, cell cultures were harvested and supernatants evaluated for presence of chemorepellent agents.

After all supernatants were collected (e.g., by timed aliquot selection), they were evaluated in the high-throughput transmigration assay described in Example 9 without further dilution.

The supernatants may be subsequently fractionated according to standard chromatographic procedures to facilitate isolation of the chemorepellent. Fractionation may be carried out by size exclusion chromatography, FPLC, HPLC, ion-exchange chromatography, hydrophobic chromatography, immune-affinity chromatography, and the like.

At each step of fractionation, chemorepulsion was measured using the method described in Example 9 for each fraction or subset thereof. Once individual measurements are made, a migration index was calculated.

The results of migration index calculations determined the fractions to be pooled and carried to the next step, thereby effecting enrichment of the amount of any putative chemorepellent agents in any subsequent pooled fraction.

After one or more steps of fractionation, the pooled fractions having the highest migration indices, (hence the highest migratory activity) are analyzed by one or two-dimensional polyacrylamide gel electrophoresis (2D-PAGE), the separated components visualized by silver or fluorescent stain and the visualized components eluted by techniques known in the art. The eluted gel spots are subjected to chemical or enzymatic fragmentation and identification using mass spectrometry, amino-acid sequencing or other techniques known to anyone skilled in the art. Alternatively, the pooled fractions with the highest migration indices could be directly analyzed by liquid chromatography (LC) mass spectrometry (MS).

Example 12

Identification of Validated Chemorepellents

Using the methods described in Examples 9-11, several classes and individual agents were identified as chemorepellents. The results are listed in Tables 3 through 15. These agents, when analyzed for cell migratory effects using the transmigration assay of Example 9 and upon calculation of repellent indices of greater than 1.2, were identified as validated chemorepellents.

Based on the repellent index, (with a threshold of 1.2 for validation), novel classes of chemorepellent agents have now been identified, none of which, to the knowledge of the inventors has been reported as having chemorepellent activity in these cells.

The results include agents such as carbohydrate binding proteins (Table 3), serpins (Table 4), bacterial cell wall components (Table 5), heat shock proteins (Table 6), natural products (Table 7), Toll-like receptor ligands (Table 8) viral factors (Table 9), semaphorins (Table 10), elastase inhibitors (Table 11), antibiotics (Table 12), muscle cell proteins (Table 13), plant cell wall components (Table 14) and chemokines (Table 15).

The repellent index for each agent was calculated from the independent assessment of three batches of donor blood from three different individuals, with each measurement from donor blood conducted in triplicate at four different concentrations of ligand. The ranges are given in the tables and covered a 1000-fold change in concentration. The repellent indices reported in Tables 3-15 represents the mean value of three donor blood samples at the concentration of ligand at which the highest activity was observed. Thus, for each listed compound, the observed chemorepulsion is likely independent of physiological differences across the donor groups and likewise the human population, suggesting strongly that induction of chemorepulsion by a validated chemorepellent is a true physiological phenomenon. Concentrations expressed in µM unless otherwise noted. It is noted that for heat killed Listeria, the concentration can only be expressed as number of cells per milliliter.

In Table 16, the repellent indices and standard deviations measured at four concentrations of selected members of the classes of compounds of Tables 3-15 are given. The standard deviations given in Table 16 represent that calculated based on one experiment (one donor) conducted in triplicate.

TABLE 3

Chemorepulsion by carbohydrate binding proteins (galectins)

| Agent | Cell Type | Accession # | Repellent Index | Concentration Range (µM) |
|---|---|---|---|---|
| Galectin-1 | Neutrophils | P09382 | 2.3 | 0.00125-1.25 |
| Galectin-2 | CD8+ | P05162 | 1.5 | 0.00125-1.25 |
| Galectin-3 | CD8+ | P17931/ BAA22164/ NP_002297 | 1.3 | 0.00125-1.25 |
|  | Neutrophils |  | 1.6 | 0.00125-1.25 |

TABLE 4

Chemorepulsion by serpins

| Agent | Cell Type | Accession # | Repellent Index | Concentration Range (µM) |
|---|---|---|---|---|
| Antithrombin III | Neutrophils | AAB40025 | 2.2 | 0.000573-0.573 |

TABLE 5

Chemorepulsion by bacterial cell wall components

| Agent | Cell Type | Accession # | Repellent Index | Concentration Range (µM) |
|---|---|---|---|---|
| Peptidoglycan from S. aureus | B cells | MDL# MFCD00212486 | 1.6 | 0.01-10 |
|  | Neutrophils |  | 8.2 | 0.01-10 |
| Lipoteichoic acid from *Bacillus subtilis* | Neutrophils | cas# 56411-57-5 | 6.5 | 0.01-10 |

TABLE 6

Chemorepulsion by heat shock proteins

| Agent | Cell Type | Accession # | Repellent Index | Concentration Range (µM) |
|---|---|---|---|---|
| Heat Shock Protein 25 | CD8+ | AAA37862 | 1.3 | 0.00125-1.25 |
|  | Neutrophils |  | 11.9 | 0.00125-1.25 |
| Heat Shock Protein 27 | Neutrophils | G01523/ AAA62175 | 4.4 | 0.00125-1.25 |
| Heat Shock Protein 32 | Neutrophils | P06762/ AAH91164 | 1.8 | 0.00125-1.25 |
| Heat Shock Protein 40 | Neutrophils | BAA08495 | 1.4 | 0.00125-1.25 |
| Heat Shock Protein 47 | CD8+ | AAP35758 | 1.4 | 0.00125-1.25 |
|  | Neutrophils |  | 1.4 | 0.00125-1.25 |
|  | B cells |  | 1.5 | 0.00125-1.25 |
| Heat Shock Protein 65 | CD8+ | AAQ64501 | 1.7 | 0.00125-1.25 |
|  | Neutrophils |  | 11.8 | 0.00125-1.25 |
| Heat Shock Protein 70 | CD4+ | AAA02807 | 4.9 | 0.00125-1.25 |
|  | CD8+ |  | 11.6 | 0.00125-1.25 |
|  | Neutrophils |  | 8.8 | 0.00125-1.25 |
| Heat Shock Protein 90 | Neutrophils | NP_005339.2/ HSP90AA1-2P/ CAD62296.1/ AAH023006.1 | 1.7 | 0.00125-1.25 |

TABLE 7

Chemorepulsion by natural products

| Ligand | Cell Type | Accession # | Repellent Index | Concentration Range (µM) |
|---|---|---|---|---|
| Genistein (soybean) | Neutrophils | Cas# 446-72-0 | 1.3 | 0.00125-1.25 |
| Resveratrol | Neutrophils | cas# 501-36-0 | 1.4 | 0.00125-1.25 |

TABLE 8

Chemorepulsion by Toll-like receptor ligands (TLR Ligands)

| Ligand | Cell Type | Accession # | Repellent Index | Concentration Range (µM)[1] |
|---|---|---|---|---|
| Pam3CSK4 | Neutrophils | Synthetic bacterial lipoprotein | 4.9 | 0.00125-1.25 |
| Heat killed *Listeria monocytogenes* | Neutrophils |  | 7.7 | $10^6$-$10^9$ Cells/ml |
| Poly(I:C) | Neutrophils | Synthetic analog of dsRNA | 1.4 | 0.01-10 µg/ml |
| *Ecoli* K12 LPS | Neutrophils |  | 8.2 | 0.01-10 µg/ml |
| *S. typhimurium* Flagellin | B cells | M11332 | 1.7 | 0.01-10 µg/ml |
|  | Neutrophils |  | 5.5 | 0.01-10 µg/ml |
| FLS-1 | Neutrophils | Synthetic lipoprotein | 6.8 | 0.01-10 µg/ml |
| ssRNA40/LyoVec | Neutrophils | ssRNA complexed with cationic lipid | 1.3 | 0.01-10 µg/ml |
| ODN2006 | Neutrophils | Synthetic oligonucleotide | 1.4 | 0.01-10 µg/ml |

TABLE 9

Chemorepulsion by viral factors

| Ligand | Cell Type | Accession # | Repellent Index | Concentration Range (μM) |
|---|---|---|---|---|
| rvCMVUL146 | CD4+ | AY183378 | 1.4 | 0.00125-1.25 |
|  | Neutrophils |  | 8.2 | 0.00125-1.25 |
| vMIP-1 | Neutrophils |  | 1.6 | 0.00125-1.25 |

TABLE 10

Chemorepulsion by semaphorins

| Ligand | Cell Type | Accession # | Repellent Index | Concentration Range (μM) |
|---|---|---|---|---|
| Semaphorin 3A | CD8+ |  | 1.3 | 0.01-10 |
|  | B cells |  | 1.6 | 0.01-10 |
| Semaphorin 3F | CD8+ |  | 1.3 | 0.01-10 |
|  | Neutrophils |  | 1.8 | 0.01-10 |

TABLE 11

Chemorepulsion by elastase inhibitors

| Ligand | Cell Type | Accession # | Repellent Index | Concentration Range (μM) |
|---|---|---|---|---|
| Elafin | CD4+ |  | 1.3 | 0.00125-1.25 |
|  | Neutrophils |  | 2.0 | 0.00125-1.25 |

TABLE 12

Chemorepulsion by macrolide or ketolide antibiotics

| Ligand | Cell Type | Accession # | Repellent Index | Concentration Range (μM) |
|---|---|---|---|---|
| Erythromycin | Neutrophils |  | 4.8 | 0.00125-1.25 |

TABLE 13

Chemorepulsion by muscle proteins

| Ligand | Cell Type | Accession # | Repellent Index | Concentration Range (μM) |
|---|---|---|---|---|
| Tropomyosin | Neutrophils |  | 1.7 | 0.00125-1.25 |

TABLE 14

Chemorepulsion by plant cell wall components

| Ligand | Cell Type | Accession # | Repellent Index | Concentration Range (μM) |
|---|---|---|---|---|
| Citrus pectin | Neutrophils |  | 1.9 | 0.00125-1.25 |

TABLE 15

Chemorepulsion by chemokines

| Ligand | Cell Type | Repellent Index | Concentration Range (μM) |
|---|---|---|---|
| CXCL1 | Neutrophils | 2.6 | 0.00125-1.25 |
| CXCL2 | Neutrophils | 1.6 | 0.00125-1.25 |
| CXCL7 | Neutrophils | 3.9 | 0.00125-1.25 |
|  | Monocytes | 1.4 | 0.00125-1.25 |
| CCL2 | B cells | 1.5 | 0.00125-1.25 |
|  | Monocytes | 1.7 | 0.00125-1.25 |
| CCL7 | Monocytes | 2.3 | 0.00125-1.25 |
| CCL8 | B cells | 2.6 | 0.00125-1.25 |
|  | Monocytes | 2.3 | 0.00125-1.25 |
| CCL11 | B cells | 2.1 | 0.00125-1.25 |
| CCL13 | Monocytes | 2.6 | 0.00125-1.25 |
| CCL15 | Monocytes | 1.4 | 0.00125-1.25 |
| CCL19 | B cells | 2.0 | 0.00125-1.25 |
|  | CD4 | 1.7 | 0.00125-1.25 |
|  | Neutrophils | 1.5 | 0.00125-1.25 |
| CCL27 | B cells | 1.4 | 0.00125-1.25 |
| CXCL1 | B cells | 1.3 | 0.00125-1.25 |

TABLE 16

Repellent indices of select chemorepellents galectin-1 induced chemorepulsion of neutrophils

| | Concentration (μM) | | | |
|---|---|---|---|---|
| | 0.00125 | 0.0125 | 0.125 | 1.25 |
| Repellent Index | 0.80 ± 0.08 | 0.96 ± 0.22 | 1.05 ± 0.14 | 3.70 ± 0.29 |

Anti-thrombin III induced chemorepulsion of neutrophils

| | Concentration (μM) | | | |
|---|---|---|---|---|
| | 0.000573 | 0.00573 | 0.0573 | 0.573 |
| Repellent Index | 1.08 ± 0.36 | 1.63 ± 0.67 | 3.17 ± 0.98 | 5.55 ± 1.71 |

Staphylococcus aureus peptidoglycan induced chemorepulsion of neutrophils

| | Concentration (μg/ml) | | | |
|---|---|---|---|---|
| | 0.01 | 0.1 | 1.0 | 10 |
| Repellent Index | 2.88 ± 1.10 | 3.10 ± 0.23 | 11.21 ± 0.46 | 6.40 ± 0.34 | heat shock protein-70 induced chemorepulsion of T lymphocytes

| | Concentration (μM) | | | |
|---|---|---|---|---|
| | 0.00125 | 0.0125 | 0.125 | 1.25 |
| Repellent Index | 0.96 ± 0.13 | 1.15 ± 0.24 | 1.65 ± 0.35 | 14.56 ± 0.61 | resveratrol induced chemorepulsion of neutrophils

| | Concentration (μM) | | | |
|---|---|---|---|---|
| | 0.00125 | 0.0125 | 0.125 | 1.25 |
| Repellent Index | 2.65 ± 0.29 | 2.80 ± 0.32 | 2.05 ± 0.28 | 1.32 ± 0.50 |

TABLE 16-continued

Repellent indices of select chemorepellents heat killed Listeria monocytogenes (HKLM) induced chemorepulsion of neutrophils

| | Number of HKLM | | | |
|---|---|---|---|---|
| | $10^6$ | $10^7$ | $10^8$ | $10^9$ |
| Repellent Index | 1.19 ± 0.49 | 3.24 ± 0.41 | 10.75 ± 0.73 | 6.38 ± 0.53 | recombinant cytomegalovirus UL146 induced chemorepulsion of neutrophils

| | Concentration (µM) | | | |
|---|---|---|---|---|
| | 0.00125 | 0.0125 | 0.125 | 1.25 |
| Repellent Index | 0.92 ± 0.44 | 1.92 ± 0.49 | 4.24 ± 0.27 | 11.65 ± 0.49 | semaphorin 3A induced chemorepulsion of B cells

| | Concentration (µM) | | | |
|---|---|---|---|---|
| | 0.00125 | 0.0125 | 0.125 | 1.25 |
| Repellent Index | 1.87 ± 0.40 | 2.07 ± 0.52 | 2.39 ± 0.71 | 2.16 ± 0.28 | elafin induced chemorepulsion of neutrophils

| | Concentration (µM) | | | |
|---|---|---|---|---|
| | 0.00125 | 0.0125 | 0.125 | 1.25 |
| Repellent Index | 1.33 ± 0.28 | 1.31 ± 0.29 | 1.48 ± 0.22 | 2.42 ± 0.52 | erythromycin induced chemorepulsion of neutrophils

| | Concentration (µM) | | | |
|---|---|---|---|---|
| | 0.00125 | 0.0125 | 0.125 | 1.25 |
| Repellent Index | 1.75 ± 0.40 | 2.29 ± 1.61 | 3.29 ± 1.11 | 6.12 ± 2.53 | tropomyosin induced chemorepulsion of neutrophils

| | Concentration (µM) | | | |
|---|---|---|---|---|
| | 0.00125 | 0.0125 | 0.125 | 1.25 |
| Repellent Index | 2.57 ± 0.73 | 2.26 ± 0.86 | 2.23 ± 0.68 | 1.67 ± 0.16 | citrus pectin induced chemorepulsion of neutrophils

| | Concentration (µM) | | | |
|---|---|---|---|---|
| | 0.00125 | 0.0125 | 0.125 | 1.25 |
| Repellent Index | 2.32 ± 1.24 | 2.35 ± 0.77 | 2.23 ± 0.88 | 2.79 ± 0.88 |

Example 13

Identification of Cells Derived from Human Cancers which Secrete Chemorepellent Agents To identify the presence of chemorepellent agents originating from human cancers, lymphoma, ovarian, prostate and breast cancer lineages were evaluated using the methods of Examples 9-11. Table 17 lists the migration index (MI) for a series of commercially available cell lines derived from human tumors. Each of these cell lines were grown in traditional cell growth media until the cultures reached confluency. Then the cells were collected, washed and resuspended by aliquoting the cells into flasks in serum-free media. Once in serum-free media, the cellular secretions in the media were collected for each cell type from a separate flask for each day for 7 consecutive days. The mixture of secretants containing putative chemorepellents was tested in the transmigration assay method of Example 9 without dilution or concentration and migration indices were calculated.

Because measurements were made across the entire time-course (i.e., each day), the daily aliquots having peak activity were identified as being those supernatants which were to be evaluated for the presence of novel chemorepellent agents. Table 17 lists the results.

TABLE 17

Production of chemorepellents by human cancer cell lines.

| Origin | Cell line | ATCC accession # | Cell type moved | Migration Index [(CR)/(SM)] | Days in culture (peak activity day) |
|---|---|---|---|---|---|
| Lung | NCI-H441 | HTB-174 | CD4+ | 1.8 | 1 |
| | | | CD8+ | 1.6 | 6 |
| | | | Neutrophils | 3.2 | 7 |
| | A549 | CCL-185 | CD4+ | 1.8 | 1 |
| | | | CD8+ | 1.6 | 5 |
| | | | Neutrophils | 3.9 | 2 |
| | NCI-H1974 | CRL-5908 | CD4+ | 1.5 | 3 |
| | | | CD8+ | 1.7 | 5 |
| | | | Neutrophils | 1.5 | 7 |
| Lymphoma | Loucy | CRL-2629 | CD4+ | 1.8 | 3 |
| | | | CD8+ | 1.6 | 2 |
| | | | Neutrophils | 2.1 | 7 |
| | H9 | HTB-176 | CD4+ | 1.6 | 1 |
| | | | CD8+ | 1.8 | 1 |
| | | | Neutrophils | 4.5 | 1 |

TABLE 17-continued

Production of chemorepellents by human cancer cell lines.

| Origin | Cell line | ATCC accession # | Cell type moved | Migration Index [(CR)/(SM)] | Days in culture (peak activity day) |
|---|---|---|---|---|---|
| | CCRF-CEM | CCL-119 | CD4+ | 1.2 | 2 |
| | | | CD8+ | 2.0 | 3 |
| | | | Neutrophils | 1.7 | 4 |
| | HuT 78 | TIB-161 | CD4+ | 1.3 | 4 |
| | | | CD8+ | 1.7 | 6 |
| | | | Neutrophils | 3.2 | 1 |
| Ovarian | ES-2 | CRL-1978 | CD8+ | 2.7 | 6 |
| | | | Neutrophils | 2.0 | 1 |
| | PA-1 | CRL-1572 | CD8+ | 1.5 | 6 |
| | | | Neutrophils | 11.7 | 2 |
| | HS 38.T | CRL-7826 | CD4+ | 1.3 | 2 |
| | | | CD8+ | 1.4 | 1 |
| | | | Neutrophils | 2.3 | 2 |
| | Caov-3 | HTB-75 | CD4+ | 1.3 | 2 |
| | | | CD8+ | 1.2 | 7 |
| | | | Neutrophils | 1.3 | 3 |
| | | | CD8+ | 1.2 | 7 |
| Prostate | PC-3 | CRL-1435 | CD4+ | 2.1 | 4 |
| | | | CD8+ | 1.5 | 7 |
| | | | Neutrophils | 2.0 | 4 |
| | 22Rv1 | CRL-2505 | CD4+ | 1.6 | 1 |
| | | | CD8+ | 11 | 3 |
| | | | Neutrophils | 1.2 | 2 |
| | LNCaP Clone FGC | CRL-1740 | CD4+ | 2.0 | 2 |
| | | | CD8+ | 1.3 | 1 |
| | DU 145 | HTB-81 | CD4+ | 1.3 | 5 |
| | | | CD8+ | 1.9 | 4 |
| Breast | SKBR3 | HTB-30 | CD4+ | 2.5 | 5 |
| | | | CD8+ | 3.1 | 5 |
| | | | Neutrophils | 3.0 | 4 |
| | BT-20 | HTB-19 | CD4+ | 1.8 | 3 |
| | | | CD8+ | 1.3 | 1 |
| | MDA-MB-157 | HTB-24 | CD4+ | 1.4 | 5 |
| | | | Neutrophils | 2.5 | 7 |
| | MDA-MB-231 | HTB-26 | CD4+ | 1.9 | 7 |
| | | | CD8+ | 1.2 | 7 |
| | | | Neutrophils | 4.8 | 7 |
| | ZR-75-1 | CRL-1500 | CD4+ | 1.4 | 3 |
| | | | Neutrophils | 2.8 | 5 |
| Colorectal | COLO 320DM | CCL-220 | CD4+ | 1.6 | 1 |
| | COLO 205 | CCL-222 | CD4+ | 1.6 | 2 |
| | | | CD8+ | 1.4 | 6 |
| | HT-29 | HTB-38 | CD4+ | 1.9 | 2 |
| | | | CD8+ | 1.6 | 1 |
| | | | Neutrophils | 2.8 | 1 |
| | Caco-2 | HTB-37 | CD4+ | 1.8 | 2 |
| | | | Neutrophils | 2.9 | 3 |
| | SW480 | CCL-228 | CD4+ | 1.6 | 2 |
| | | | CD8+ | 1.7 | 3 |
| | | | Neutrophils | 3.2 | 4 |
| Melanoma | WM-266-4 | CRL-1676 | CD4+ | 1.9 | 1 |
| | | | CD8+ | 1.3 | 4 |
| | | | Neutrophils | 3.2 | 5 |

Mixtures whose migration index is equal to or greater than 1.2, are considered to contain at least one "validated conditioned chemorepellent."

From the Table it is evident that, at the peak activity time points noted, certain human cancer cell lines do secrete chemorepellents into the conditioned media which trigger or induce movement of at least neutrophils, CD4+, and CD8+ cells.

Studies are currently underway to determine the identity of these chemorepellents.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of ameliorating an inflammatory response in a human subject comprising:
    administering a chemorepellant to a site of inflammation in said subject, wherein said chemorepellent is administered in an amount effective to induce negative chemotaxis of at least a portion of a population of neutrophils from the site of inflammation, wherein the chemorepellent is galectin-3.

2. A method of inducing negative chemotaxis in human neutrophils comprising contacting said human neutrophils with a chemorepellent in an amount sufficient to induce negative chemotaxis along a concentration gradient wherein the chemorepellent is galectin-1 or galectin-3, and wherein negative chemotaxis is induced in vitro.

* * * * *